US006046384A

United States Patent [19]
McMaster et al.

[11] Patent Number: 6,046,384
[45] Date of Patent: *Apr. 4, 2000

[54] PAPAYA RINGSPOT VIRUS NIA PROTEASE GENE

[75] Inventors: J. Russell McMaster, Kenosha, Wis.; Maury L. Boeshore, Wauconda, Ill.; David M. Tricoli, Davis, Calif.; John F. Reynolds, Davis, Calif.; Kim J. Carney, Davis, Calif.; Jerry L. Slighton, Kalamazoo, Mich.; Dennis Gonsalves, Geneva, N.Y.

[73] Assignees: Seminis Vegetable Seeds, Inc., Saticoy, Calif.; Cornell Research Foundation, Inc., Ithaca, N.Y.

[*] Notice: This patent is subject to a terminal disclaimer.

[21] Appl. No.: 08/860,483

[22] PCT Filed: Jun. 7, 1995

[86] PCT No.: PCT/US95/07185

§ 371 Date: Nov. 3, 1997

§ 102(e) Date: Nov. 3, 1997

[87] PCT Pub. No.: WO96/21033

PCT Pub. Date: Jul. 11, 1996

[51] Int. Cl.$^7$ ...................................................... A01H 1/00
[52] U.S. Cl. .......................... 800/279; 800/288; 800/294; 536/23.2; 536/23.72; 536/24.1; 435/252.3; 435/370.1; 435/468; 435/469
[58] Field of Search ................................... 800/205, 280, 800/301, 279, 288, 294; 536/23.2, 24.1, 23.72; 435/320.1, 172.3, 69.1, 419, 430, 52.3, 468, 469

[56] References Cited

U.S. PATENT DOCUMENTS 5,349,128  9/1994  Quemada et al. ....................... 800/301
5,589,612  12/1996  Jilka et al. .............................. 800/280

OTHER PUBLICATIONS

Wang, C.H. et al., *The American Phytopathologial Society*, 84:10, 1205–1210, (1994).

Maureen M.M. Fitch, Richard M. Manshardt, Dennis Gonsalves, Jerry L. Slightom and John C. Sanford, Virus Resistant Papaya Plants Derived from Tissues Bonbarded With The Coat Protein Gene of Papaya Ringspot Virus, *BioTechnology* 10:1466–1472 (Nov. 1992).

John H. Fitchen and Roger N. Beachy, Genetically Engineered Protection Against Viruses In Transgenic Plants, *Annu. Rev. Microbiol.* 47:739–63, (1993).

Indu. B. Maiti, John F. Murphy, John g. Shaw, and Arthur G. Hunt, Plant biology, Plants that express a potyvirus proteinase gene are resistant to virus infection, *Proc. Natl. Acad. Sci. USA*, 90:6110–6114, (Jul. 1993).

Hector Quemada, Brigitte L'Hostis, Dennis Gonsalves, Bene M. Reardon, Robert Heinrikson, Ernest L. Hiebert, Leang C. Sieu and Jerry L. Slightom, The nucleotide sequences of the 3'–terminal regions of papaya ringspot virus strains W and P, *Journal of General Virology* 71:203–210, (1990).

P. F. Tennant, C. Gonsalves, K,–S, Ling, M. Fitch, R. Manshartd, J.L. Slightom, and D. Gonsalves, Differential Protection Against Papaya Ringspot Virus Isolates in Coat Protein Gene Transgenic Papaya and Classically Cross–Protected Papaya, *The American Phyto–Pthological Society*, 84:1359–1366 (1994).

S,–D. Yeh, D. Gonsalves, and R. Provvidenti, Comparative Studies on Host Range and Serology of Papaya Ringspot Virus and Watermelon Mosaic Virus 1, *The American Phytopathological Society*, 74:1081–1085 (1984).

Alexander R. van der Krol, Peter E. Lenting, Jetty Veenstra, Ingrid M van der Meer, Ronald E. Koes, Anton G.M. Gerats, Joseph N.M. Mol & Antoine R. Stuitje, An anti–sense chalcone synthase gene in transgenic plants inhibits flower pigmentation, *Nature*, 333:866–869, (Jun. 30, 1988).

C.J.S. Smith, C.F. Watson, J.Ray, C.R. Bird, P.C. Moris, W. Schuch, &&–D. Grierson, Antisense RNA inhibition of polygalacturonase gene expression in transgenic tomatoes, *NatureI*, 334 25:724–726 (Aug. 1988).

Michael Bevan, Wayne M. Barnes and Mary–Dell Chilton, Structure and transcription of the nopaline synthase gene region of T–DNA *Nucleic Acids Research*, 11(2):369–385, (1982).

A. Depicker, S. Stachel, P.Dhaese, P. Zambryski, and H.M. Goodman, Nopaline Synthase: Transcript Mapping and DNA Sequence, *Journal of Molecular and Applied Genetics*, 1(6):561–573, (1982).

Jerzy Paszkowski, Raymond D. Shillito, Michael Saul, Vaclav Mandak, Thomas Hohn, Barbara Hohn and Ingo Potrykus, Direct gene transfer to plants, *The EMBO Journal*, vol. 3(12):2717–2722,(1984).

Anne Crossway, Janette V. Oakes, Jonathan M. Irvine, Barney Ward, Vic C Knauf, and C.K. Shewmaker, Integration of foreign DNA following microinjection of tobacco mesophyll protoplasts, *Mol. Gen. Genet* 202:179–185, (1986).

Michael Fromm, Loverine P. Taylor, and Virginia Walbot, Expression of genes transferred into monocot and dicot plant cells by electropporation *Proc. Natl. Acad. Sci. USA*, 82:5824–5828, (Sep. 1985) Genetics.

T.M. Klein, E.D. Wolf, R. Wu & J.C. Sanford, High–velocity microprojectiles for delivering nucleic acids into living cells, *Nature*, 327 &:70–73, (May 1987).

S. Luis & R. Hanshardt, Field Test of Virus Resistance In Transgenic Papayas, 91$^{st}$ Annual Meeting of the American Society for Horticultural Science Hortscience, 29:483(1994).

(List continued on next page.)

Primary Examiner—Nancy Degen
Assistant Examiner—Irem Yucel
Attorney, Agent, or Firm—Rockey, Milnamow & Katz, Ltd.

[57] ABSTRACT

NIa protease genes of papaya ringspot virus strains FLA83 and USA P-type (HA-attenuated strain) are provided.

25 Claims, 18 Drawing Sheets

OTHER PUBLICATIONS

Shigetou Nanba, Kaishu Ling, Carol Gonsalves, Dennis Gonsalves and Jerry L. Slighton, Expression of the gene encoding the coat protein of cucumber mosaic virus (CMV) strain WL appears to provide protection to tobacco plants against infection by several different CMV strains, *Gene*, 107:181–188, (1991).

Ms. Bateson and J. Dale, The nucleotide sequence of the coat protein gene and 3' untranslated region of papaya ringspot virus type W. (Aust), *Arch. Virol.* 123:101–109, (1992).

Marion F. Bateson, Juliane Henderson, Woravan Chaleeprom, Adrian J. Gibbs and James L. Dale, Papaya ringspot potyvirus: isolate variability and the origin of PRSV type P (Australia), *Journal of Gneeral Virology*, 75:3547–3553, 1994).

Baker, C.A., Lecoq, H, Purcifull, D.E., Serological and Biological Variability Among Papaya Ringspot Virus Type–W Isolates in Florida, Phytopathology Halles, 81(7):722–728 (1991).

Yeh, Shyi–Dong, Jan, Chu–Hui, Chiang, Chu–Hui, Doony, Tzyy–Jye, Chen, Ming–Cheng, Chung, Bau, Huey–Jiunn, Complete nucleotide sequence and genetic organization of papaya ringspot virus RNA *J. Gen. Vir.* 73:2531–2541 (1992).

Bateson, Marion F., Henderson, Juliane, Chaleeprom, Worawan, Gibbs. Adrian J. Papya ringspot potyvirus: isolate variability and the origin of PRSV type P (Australia) *Journal of General Virology,* 75:3547–3553 (1994).

Indu B. Maiti, and Arthur G. Hunt, Keystone Sympusium on Crop Improvement via Biotechnology: An International Perspective; Expression of the Tobacco Vein Mottling Virus Nuclear Inclusion Protein (NIa) Gene in Tobacco, *J Cell Biochem., Suppl.* 16F, 217(1992).

D.E. Purciful and E. Hiebert, Serological Distinction of Watermelon Mosaic Virus Isolates, *The American Society Phytopathological,* 692(2):112–116,(1979).

FIG. 2A

```
       NcoI                                                    EcoRI
                                RMM354 --> 5' GCTATGACAGGAATTCACTGGCCTAA
       CCATGGGCTTCTCTCTCC
  1    CCATGGGCTTCTCTCTCCTTGGTATCATAAACACTATCCAGAGTAGATATTTAGTTGATCATTCAGTTGAGAATATCAGAAAGCTTCAACTAGCGAAGGC    100
       MetGlyPheSerLeuLeuGlyIleIleAsnThrIleGlnSerArgTyrLeuValAspHisSerValGluAsnIleArgLysLeuGlnLeuAlaLysAl
        M  G  F  S  L  L  G  I  I  N  T  I  Q  S  R  Y  L  V  D  H  S  V  E  N  I  R  K  L  Q  L  A  K  A

101  CCAGATTCAACAACTTGAAGCTCATGTCCAAGAGAACAATGTTGGAAATTTAATTCAATCTCTTGGTCTGTTATCATCAAGGTGTTGAT              200
       aGlnIleGlnGlnLeuGluAlaHisValGlnGluAsnAsnValGlyAsnLeuIleGlnSerLeuGlyLeuLeuSerLeuGlyValArgAlaValTyrHisGlnGlyValAsp
        Q  I  Q  Q  L  E  A  H  V  Q  E  N  N  V  G  N  L  I  Q  S  L  G  A  V  R  A  V  Y  H  Q  G  V  D
                                                                                                    CI | VPg

201  GGAGTCAAGCACATAAAGCGAGAGTTGGGCTTGAAAGGAGTTTGGGATGGTTCATTAATGATCAAGGATCGAATTGTATGCGGTTTCACAATGGCTGGTG    300
       GlyValLysHisIleLysArgGluLeuGlyLeuLysGlyValTrpAspGlySerLeuMetIleLysAspArgIleValCysGlyPheThrMetAlaGlyG
        G  V  K  H  I  K  R  E  L  G  L  K  G  V  W  D  G  S  L  M  I  K  D  R  I  V  C  G  F  T  M  A  G  G

301  GTGCAATGCTCTTGTACCAACACTTTCGTGATAAGCTTACAAATGTACATGTGTTCACCAAGTTTCTCGCGACAACGACAAAAGTTACGATTAA        400
       lyAlaMetLeuLeuTyrGlnHisPheArgAspLysLeuThrAsnValHisValPheHisGlnGlyPheSerAlaArgGlnArgGlnLysLeuArgPheLy
        A  M  L  L  Y  Q  H  F  R  D  K  L  T  N  V  H  V  F  H  Q |G  F  S  A  R  Q  R  Q  K  L  R  F  K
                                                                    VPg|NIa

401  GTCAGCAGCAAATGCTAAGCTTGGTCGAGAGTCTATGGAGACGGGACACTATTCGAGAAGCATACACAGATTATTCGGAAGCACTAGATCGAAGAAG      500
       sSerAlaAlaAsnAlaLysLeuGlyArgGluValTyrPheGlyLysAspAspGlyThrIleGluHisTyrPheGlyGluAlaTyrThrLysLysGlyAsnLysLys
        S  A  A  N  A  K  L  G  R  E  V  Y  G  D  D  G  T  I  E  H  Y  F  G  E  A  Y  T  K  K  G  N  K  K

501  GGAAAGATGCATGGCATGGTGTTAAAACGAGAAAGTTCGTTGCAACATATGGATTTAAACCAGAGGATTATTCATACGTGCGGTACTTGGATCCTTTAA    600
       GlyLysMetHisGlyMetValLysThrArgLysPheValAlaThrTyrGlyPheLysProGluAspTyrSerTyrValArgTyrLeuAspProLeuT
        G  K  M  H  G  M  G  V  K  T  R  K  F  V  A  T  Y  G  F  K  P  E  D  Y  S  Y  V  R  Y  L  D  P  L  T
```

FIG. 2B

```
601 CAGGTGAGACTTTGGATGAAAGCCCACAGACTGACATCTCAATGGTCGCAAGAACATTTGTTGATATTCGGAGTAAATATTCGAGACAGCTTCGA   700
    hrGlyGluThrLeuAspGluSerProGlnThrAspIleSerMetValGlnHisPheGlyAspIleArgSerLysTyrLeuAspSerAspSerPheAs
     G  E  T  L  D  E  S  P  Q  T  D  I  S  M  V  Q  E  H  F  G  D  I  R  S  K  Y  L  D  S  D  S  F  D

701 CAGGCAGGCTTTAATAGCAACAATACAATTAAGGCCTATTATGTCCGAAGACAGCATTGGAAGTCGATTGACACCGCATAACCCTCTG   800
    pArgGlnAlaLeuIleAlaAlaAsnThrIleLysAlaTyrTyrValArgAsnSerAlaLysThrAlaLeuGluValAspLeuThrProHisAsnProLeu
     R  Q  A  L  I  A  N  N  T  I  K  A  Y  Y  V  R  N  S  A  K  T  A  L  E  V  D  L  T  P  H  N  P  L

801 AAAGTTTGTGACAACAAATTGACTATTGCAGGATTCCTGATAGAGAAGTCGAACTGAGACAAACAGGCCCAGCAGAACTATTCAAGCCGATCAAGTTC   900
    LysValCysAspAsnLysLeuThrIleAlaGlyPheProAspArgGluAlaGluLeuArgGlnThrGlyProAlaArgThrIleGlnAlaAspGlnValP
     K  V  C  D  N  K  L  T  I  A  G  F  P  D  R  E  A  E  L  R  Q  T  G  P  A  R  T  I  Q  A  D  Q  V  P

901 CACCACCTTCGAAATCAGTTCATCACGAAGGAAAAAGTCTTTGTCAAGGTATGAGAAATTACAATGCATAGCTTCCGTGGTTTGCCATTGAAAAACAC   1000
    roProProSerLysProSerValHisHisGluGlyLysLeuCysGlnGlyMetArgAsnTyrAsnGlyIleAlaSerValValCysHisLeuLysAsnTh
     P  P  P  S  K  S  V  H  H  E  G  K  S  L  C  Q  G  M  R  N  Y  N  G  I  A  S  V  V  C  H  L  K  N  T

1001 ATCGGAGATGGGAGAAGCCTATTTGGAATCGGATATAACTCGTTCATCATTACAAACCGACATTGTTCAAAGAAAATAATGTGAACTTATAGTGAAA   1100
     rSerGlyAspGlyArgSerLeuPheGlyIleGlyTyrAsnSerPheIleIleIleThrAsnArgHisLeuPheLysGluAsnAsnGlyGluLeuIleValLys
      S  G  D  G  R  S  L  F  G  I  G  Y  N  S  F  I  I  T  N  R  H  L  F  K  E  N  N  G  E  L  I  V  K

1101 TCCCAACACGGCAAGTTTGTTGTCAAGAACACCTCAACTCTCGAATTGCTCCAGTTGGAAAAACTGATCTTTTGATAATTCGGATGCCGAAAGACTTTC   1200
     SerGlnHisGlyLysPheValValLysPheValValLysAsnThrSerThrLeuArgIleAlaProValGlyLysThrAspLeuLeuIleIleArgMetProLysAspPheP
      S  Q  H  G  K  F  V  V  K  N  T  S  T  L  R  I  A  P  V  G  K  T  D  L  L  I  I  R  M  P  K  D  F  P

1201 CTCCATTCCATAGAGCTAGGTTTAGGGCCATGAAAGCTGGAGACAAGGTTTGCATGATCGGTGTTGACTACCAAGAGAATCATATTGCGAGCAAAGT   1300
     roPheHisSerArgAlaArgPheAlaMetLysAlaGlyAspLysValCysMetIleGlyValAspTyrGlnGluAsnHisIleAlaSerLysVa
      P  F  H  S  R  A  R  F  A  M  K  A  G  D  K  V  C  M  I  G  V  D  Y  Q  E  N  H  I  A  S  K  V
```

FIG. 2C

```
1301 ATCTGAAACTTCTATTATCAGTGAGGGCACGGAGAGTTTGATGCCATTGGATATCCACGAATGATGTGATTGCGTAATCCACTAGTAGTGTTCA    1400
     lSerThrSerIleIleSerGluGluGlyThrGlyGluPheGlyCysHisTrpIleSerHisThrAsnAspGlyAspCysGlyAsnProLeuValSerVal
        S   E   T   S   I   I   S   E   G   T   G   E   F   G   C   H   W   I   S   T   N   D   G   C   G   N   P   L   V   S   V   S

1401 GATGGTTTCATTGTTGGCTTGCACATAGTTTGTCGACACTCAACGGAAATCAAAATTCTTCGCTAAAATACCCGCAATTTGAAGAAAAGGTCCTGAGGA    1500
     AspGlyPheIleValGlyLeuHisSerLeuSerThrSerThrGlyAsnPheAsnGlnAsnPheAlaAlaLysIleProAlaGlnPheGluGluLysValLeuArgL
        D   G   F   I   V   G   L   H   S   L   S   T   S   T   G   N   Q   N   F   F   A   K   I   P   A   Q   F   E   E   K   V   L   R   K

1501 AAATTGATGAATTAACATGGAGCAAAACACTGAGCTACACATATTAATGAACTGAGTGTGGGAGCTCTTAAGGTGTGGAAAGTCGTCCCGAAGCAATTTT    1600
     ysIleAspGluLeuThrTrpSerLysHisTrpSerLysTyrAsnIleAsnGluLeuSerTrpGlyAlaLeuLysValTrpGluSerArgProGluAlaIlePh
        I   D   E   L   T   W   S   K   H   W   S   Y   N   I   N   E   L   S   W   G   A   L   K   V   W   E   S   R   P   E   A   I   F

1601 TAATGCGCAAAAGGAAGTCAACCAATTGAATGTTTTTGAGCAAAGTGTAGTCGTTGGCTCTTGACAAATTGAAGGCTCTTGAAGGGTGTAAGTTCC    1700
     eAsnAlaGlnLysGluValAsnGlnLeuAsnValPheGluGlnSerGlyArgTrpLeuPheAspLysLeuPheAspLysLeuHisGlyAsnLeuLysGlyValSerSer
        N   A   Q   K   E   V   N   Q   L   N   V   F   E   Q  |S   G   S   R   W   L   F   D   K   L   H   G   N   L   K   G   V   S   S
                                                              NIa|NIb
                                                                         RMM355 <-- 3' CACACTACTTATCCGGTACCAAAGAACCTAGTGAATACCC
                                                                                                    NcoI      BamHI

1701 GCTTCTAGCAATTTGGTGACAAAGCACGTTGTTAAAGGCATTTGTCCCTCTCTTCAGGAACTATCCGAGTGTGATGAATAGGCCCATGG    1789
     AlaSerSerAsnLeuValThrLysHisValValLysGlyIleCysProLeuPheArgAsnTyrLeuGluCysAspGluEndAlaHis
        A   S   S   N   L   V   T   K   H   V   V   K   G   I   C   P   L   F   R   N   Y   L   E   C   D   E   *   A   H
```

FIG. 3A

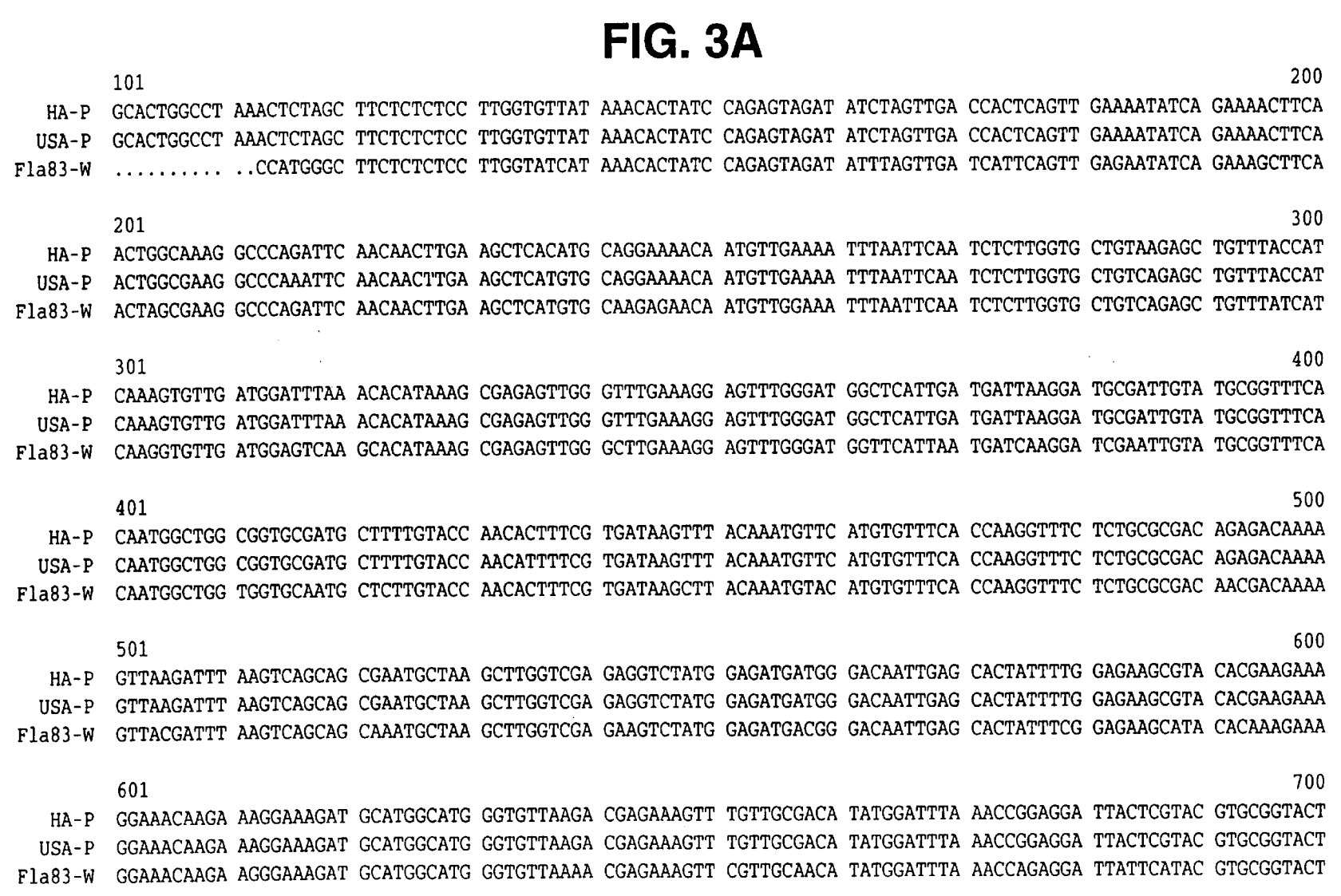

```
        101
HA-P    GCACTGGCCT AAACTCTAGC TTCTCTCTCC TTGGTGTTAT AAACACTATC CAGAGTAGAT ATCTAGTTGA CCACTCAGTT GAAAATATCA GAAAACTTCA
USA-P   G

FIG. 3B

```
            701
HA-P    TGGACCCTTT AACAGTGAG ACTTTGGATG AAAGCCCACA GACTGATATC TCAATGGTGC AAGATCATTT TAGTGATATT CGGAGAAAGT ACATGGATTC
USA-P   TGGACCCTTT AACAGTGAG ACTTTGGATG AAAGCCCACA GACTGATATC TCAATGGTGC AAGATCATTT TAGTGATATT CGGAGAAAGT ACATGGATTC
Fla83-W TGGATCCTTT AACAGTGAG ACTTTGGATG AAAGCCCACA GACTGACATC TCAATGGTGC AAGAACATTT TGGTGATATT CGGAGTAAAT ATTTGGATTC 801                                                                                                900
HA-P    AGACAGCTTC GATAGGCAGG CTTTAATAGC AAACAATACA ATTAAGGCTT ATTATGTCCG AAACTCCGCG AAGGCAGCAT TGGAAGTCGA TCTGACACCG
USA-P   AGACAGCTTC GATAGGCAGG CTTTAATAGC AAACAATACA ATTAAGGCTT ATTATGTCCG AAACTCCGCG AAGGCAGCAT TGGAAGTCGA TCTGACACCG
Fla83-W AGACAGCTTC GACAGGCAGG CTTTAATAGC AAACAATACA ATTAAGGCCT ATTATGTCCG AAACTCCGCG AAGACAGCAT TGGAAGTCGA TTTGACACCG 901                                                                                                1000
HA-P    CACAACCCTC TCAAAGTTTG TGACAATAAA TTGACCATTG CAGGATTTCC TGACAGGGAA GCTGAGCTAA GACAAACAGG CCCGCCCAGA ACTATTCAAG
USA-P   CACAACCCTC TCAAAGTTTG TGACAATAAA TTGACCATTG CAGGATTTCC TGACAGGGAA GCTGAGCTGA GACAAACAGG CCCGCCCAGA ACTATTCAAG
Fla83-W CATAACCCTC TGAAAGTTTG TGACAACAAA TTGACTATTG CAGGATTTCC TGATAGAGAA GCTGAACTGA GACAAACAGG CCCAGCCAGA ACTATTCAAG 1001                                                                                               1100
HA-P    TAGATCAAGT GCCACCACCC TCGAAATCAG TTCATCACGA AGGAAAAAGT CTTTGTCAAG GCATGAGAAA TTACAATGGC ATAGCTTCTG TGGTTTGCCA
USA-P   TAGATCAAGT GCCACCACCC TCGAAATCAG TTCATCACGA AGGAAAAAGT CTTTGTCAAG GCATGAGAAA TTACAATGGC ATAGCTTCTG TGGTTTGCCA
Fla83-W CCGATCAAGT TCCACCACCT TCGAAATCAG TTCTATCACGA AGGAAAAAGT CTTTGTCAAG GTATGAGAAA TTACAATGGC ATAGCTTCCG TGGTTTGCCA 1101                                                                                               1200
HA-P    TTTGAAAAAC ACATCAGGAA AGGGGAAGAG CTTGTTTGGA ATTGGATATA ATTCATTCAT CATTACCAAC CGACATTTGT TCAAGGAGAA TAATGGTGAA
USA-P   TTTGAAAAAC ACATCAGGAA AGGGAAAGAG CTTGTTTTGA ATTGGATATA ATTCATTCAT CATTACCAAC CGACATTTGT TCAAGGAGAA TAATGGTGAA
Fla83-W CCGATCAAGT ACATCGGGAG ATGGGAAGAA .CCTATTTGA ATCGGATATA ACTCGTTCAT ACTCATTGTT CATTACAAAC CGACATTTGT TCAAAGAAAA TAATGGTGAA 1201                                                                                               1300
HA-P    CTTATAGTGA AATCCCAACA CGGTAAGTTT ATTGTCAAGA ACACCACAAC ACTCCAAATT GCTCCAGTTG GAAAGACTGA TCTTTTAATT ATTCGGATGC
USA-P   CTTATAGTGA AATCCCAACA CGGTAAGTTT ATTGTCAAGA ACACCACAAC ACTCCGAATT GCTCCAGTTG GAAAGACTGA TCTTTTAATT ATTCGGATGC
Fla83-W CTTATAGTGA AATCCCAACA CGGCAAGTTT GTTGTCAAGA ACACCTCAAC GCTCCGAATT GCTCCAGTTG GAAAAACTGA TCTTTTGATA ATTCGGATGC
```

FIG. 3C

```
          1301
HA-P      CGAAAGATTT TCCTCCATTC CATAGCAGAG CTAGGTTTAG GGCCATGAAA GCTGGGGACA AGGTTTGCAT GATAGGTGTT GACTACCAAG AGAATCATAT
USA-P     CGAAAGATTT TCCTCCATTC CATAGCAGAG CTAGGTTTAG GGCCATGAAA GCTGGGGACA AGGTTTGCAT GATAGGTGTT GACTACCAAG AGAATCATAT
Fla83-W   CGAAAGACTT TCCTCCATTC CATAGTAGAG CTAGGTTTAG GGCCATGAAA GCTGGAGACA AGGTTTGCAT GATCGGTGTT GATCGGTGTT GACTACCAAG AGAATCATAT
                                                                                                                    1400

1401
HA-P      CGCGAGCAAA GTATCTGAAA CCTCTATCAT CAGTGAGGGC ACGGGAGATT TTGGATGCCA CTGGATATCC ACGAATGACG GTGATTGCGG TAATCCTTTA
USA-P     CGCGAGCAAA GTATCTGAAA CCTCTATCAT CAGTGAGGGC ACGGGAGATT TTGGATGCCA CTGGATATCC ACGAATGACG GTGATTGCGG TAATCCTTTA
Fla83-W   TGCGAGCAAA GTATCTGAAA CTTCTATTAT CAGTGAGGGC ACGGGAGAGT TTGGATGCCA CTGGATATCC ACGAATGATG GTGATTGCGG TAATCCACTA
                                                                                                                    1500

1501
HA-P      GTTAGTGTTT CAGATGGTTT TATTGTCGGC TTGCATAGTT TGTCGACATC AACTGGAGAT CAAAATTTCT TTGCCAAAAT ACCCGCACAA TTTGAAGAAA
USA-P     GTTAGTGTTT CAGATGGTTT TATTGTCGGC TTGCATAGTT TGTCGACATC AACTGGAGAT CAAAATTTCT TTGCTAAAAT ACCCGCACAA TTTGAAGAAA
Fla83-W   GTTAGTGTTT CAGATGGTTT CATTGTTGGC TTGCATAGTT TGTCGACATC AACCGGAAAT AATATTAATG AACTGAGTTG TCGCTAAAAT ACCCGCACAA TTTGAAGAAA
                                                                                                                    1600

1601
HA-P      AGGTCCTTAG GAAGATTGAT GATTTAACTT GGAGCAAACA CTGGAGCTAT AATATTAATG AACTGAGTTG GGGAGCTCTC AAAGTGTGGG AAAGTCGGCC
USA-P     AGGTCCTTAG GAAGATTGAT GATTTAACTT GGAGCAAACA CTGGAGCTAT AATATTAATG AACTGAGTTG GGGAGCTCTC AAAGTGTGGG AAAGTCGGCC
Fla83-W   AGGTCCTGAG GAAAATTGAT GAATTAACAT GGAGCAAACA CTGGAGCTAC AATATTAATG AACTGAGTTG GGGAGCTCTT AAGGTGTGGG AAAGTCGTCC
                                                                                                                    1700

1701
HA-P      CGAAGCAATT TTTAACGCAC AAAAGGAAGT TAATCAATTG AATGTTTTCG AGCAAAGTGG TGGTCGTTGG CTCTTTGACA AATTACACGG CAATTTGAAA
USA-P     CGAAGCAATT TTTAACGCGC AAAAGGAAGT TAATCAATTG AATGTTTTCG AGCAAAGTGG TAGTCGTTGG CTCTTTGACA AATTACACGG CAATTTGAAA
Fla83-W   CGAAGCAATT TTTAATGCGC AAAAGGAAGT CAACCAATTG AATGTTTTTG AGCAAAGTGG TAGTCGTTGG CTCTTCGACA AATTACACGG CAATTTGAAG
                                                                                                                    1800
```

FIG. 3D

```
        1801                                                                                                              1900
HA-P    GGAGTTAGCT CCGCTCCTAG CAATTTGGTG ACAAAGCACG TTGTTAAAGG AATTTGTCCT CTTTTCAGGA ACTATCTCGA GTGTGATGAA GAGGCTAAAG
USA-P   GGAGTTAGCT CCGCTCCTAG CAATTTGGTG ACAAAGCACG TTGTTAAAGG AATTTGTCCT CTTTTCAGGA ACTATCTCGA GTGTGATGAA GAGGCTAAAG
Fla83-W GGTGTAAGTT CCGCTTCTAG CAATTTGGTG ACAAAGCACG TTGTTAAAGG CATTTGTCCT CTCTTCAGGA ACTATCTCGA GTGTGATGAA TAGCCCCATG 1901                                                                                                              2000
HA-P    CTTTCTTTAG TCCACTTATG GGTCACTACA TGAAGAGTGT TCTGAGCAAG GAAGCGTACA TTAAGGATTT ATTGAAATAT TCAAGTGATA TTGTCGTTGG
USA-P   CTTTCTTTAG TCCACTTATG GGTCACTACA TGAAGAGTGT TCTGAGCAAG GAAGCGTACA TTAAGGATTT ATTGAAATAT TCAAGTGATA TTGTCGTTGG
Fla83-W G..........
```

FIG. 4A

```
                                                                                                          Q/G
                                                                                                          CI/VPg
            *                    *                    *              *               *                   *        100
Fla83-W    ............ ............ ............ ............ ............ ............ ............ ............
USA-P      ............ ............ ............ ............ MGFSLL GLINTIQSRY LVDHSVENIR KLQLAKAQIQ QLEAHVQENN VGNLIQSLGA

FIG. 4B

```
          *  *                                                                                   *                                      500
Fla83-W   TSTLRIAPVG KTDLLIIRMP KDFPPFHSRA RFRAMKAGDK VCMIGVDYQE NHIASKVSET SIISEGTGEF GCHWISTNDG DCGNPLVSVS DGFIVGLHSL
 USA-P    TTTLRIAPVG KTDLLIIRMP KDFPPFHSRA RFRAMKAGDK VCMIGVDYQE NHIASKVSET SIISEGTGDF GCHWISTNDG DCGNPLVSVS DGFIVGLHSL
  HA-P    TTTLQIAPVG KTDLLIIRMP KDFPPFHSRA RFRAMKAGDK VCMIGVDYQE NHIASKVSET SIISEGTGDF GCHWISTNDG DCGNPLVSVS DGFIVGLHSL
           14                                                                                   15
                                                                                                   Q/S
          501  *                      *                                                          NIa/NIb                        600
Fla83-W   STSTGNQNFF AKIPAQFEEK VLRKIDELTW SKHWSYNINE LSWGALKVWE SRPEAIFNAQ KEVNQLNVFE QSGSRWLFDK LHGNLKGVSS ASSNLVTKHV
 USA-P    STSTGDQNFF AKIPAQFEEK VLRKIDDLTW SKHWSYNINE LSWGALKVWE SRPEAIFNAQ KEVNQLNVFE QSGSRWLFDK LHGNLKGVSS APSNLVTKHV
  HA-P    STSTGDQNFF AKIPAQFEEK VLRKIDDLTW SKHWSYNINE LSWGALKVWE SRPEAIFNAQ KEVNQLNVFE QSGGRWLFDK LHGNLKGVSS APSNLVTKHV
              16                      17

601
Fla83-W   VKGICPLFRN YLECDE*AH.
 USA-P    VKGICPLFRN YLECDEEAKA
  HA-P    VKGICPLFRN YLECDEEAKA
```

FIG. 5A

```
      NcoI                        RMM354-->  5' GCTATGACAGAATTCACTGGCCTAA
      CCATGGGCTTCTCTCTCC                                    EcoRI

1   CCATGGGCTTCTCTCTTGGTGTTATAAACACTATCCAGAGATAGATATCTAGTTGACCACTCAGTTGAAAAATATCAGAAAAACTTCAACTGGCCGAAGGC
      MetGlyPheSerLeuLeuGlyValIleAsnThrIleGlnSerArgTyrLeuValAspHisSerValGluAsnIleArgLysLeuGlnLeuAlaLysAl
      M  G  F  S  L  L  G  V  I  N  T  I  Q  S  R  Y  L  V  D  H  S  V  E  N  I  R  K  L  Q  L  A  K  A

101   CCAAATTCAACACTTGAAGCTCATGTGCAGGAAAACAATGTTGAAAATTAATTCAATCTTCTTGGTGTCTGTCAGAGCTGTTACCATCAAAGTGTTGAT
      aGlnIleGlnLeuGlnLeuAlaHisValGlnGluAsnAsnValGluAsnLeuIleGlnSerLeuLeuAlaValArgAlaValTyrHisGlnSerValAsp
      Q  I  Q  Q  L  E  A  H  V  Q  E  N  N  V  E  N  L  I  Q  S  L  L  G  A  V  R  A  V  Y  H  Q  S  V  D
                                                                                                CI   VPg

201   GGATTAAACACATAAAGCGAGAGTTGGGTTTGAAAGGAGTTGAAAGGAGTTGGTGTTGAAAGGAGTTGGAGTTGAAGGATGGCTCATTGATGATTAAGGATGGCTATGCGGTTCACAATGGCTGGCG
      GlyPheLysHisIleLysArgGluLeuGlyLeuLysGlyValTrpAspGlySerLeuMetIleLysAspAlaIleValCysGlyPheThrMetAlaGlyG
      G  F  K  H  I  K  R  E  L  G  L  K  G  V  W  D  G  S  L  M  I  K  D  A  I  V  C  G  F  T  M  A  G  G
                           EcoRI      NcoI
      RMM333 --> 5'   TTTACAGAATTCCCCATGGTAAACAT GGTTTCTCTGCGCGACAGACAAAAGTTAA

301   GTGCCGATGCTTTGTACCAACATTTCTGTGATAAGTTTACAAATGTTCATGTGTTCACCAAGGTTTCATCCAAGAGACAAAAGTTAAGATTAA
      lyAlaMetLeuLeuTyrGlnHisPheArgAspLysPheThrAsnValPheHisGlnGlyPheSerAlaArgGlnArgGlnLysLeuArgPheLy
      A  M  L  L  Y  Q  H  F  R  D  K  F  T  N  V  F  H  Q  G  F  S  A  R  Q  R  Q  K  L  R  F  K
                                                         M  V  N  M  V  S  L  R  D  R  D  K  S  *
                                                         VPg|NIa

401   GTCAGCAGCGAATGTCTAAGCTTGGTCGAGAGGTCTATGGAGATGATGGAGACAATTTTGGAGAAGCGTACACGAAGAAGAAAAGAAACAAGAAA
      sSerAlaAlaAsnAlaLysLeuGlyArgGluValTyrGlyAspAspGlyThrIleGluHisTyrPheGlyGluAlaTyrThrLysLysGlyAsnLysLys
      S  A  A  N  K  L  G  R  E  V  Y  G  D  D  G  T  I  E  H  Y  F  G  E  A  Y  T  K  K  G  N  K  K

501   GGAAAGATGCATGGCATGGGCTTAAGACACGGAGAAAGTTGTTGCCACATATGGATTTAAACCGGAGTACTCCTACGTGCCGTACTTGACCCTTTAA
      GlyLysMetHisGlyMetGlyValLysThrArgLysPheValAlaThrTyrGlyPheLysProGluAspTyrSerTyrValArgTyrLeuAspProLeuT
      G  K  M  H  G  M  G  V  K  T  R  K  F  V  A  T  Y  G  F  K  P  E  D  Y  S  Y  V  R  Y  L  D  P  L  T
```

FIG. 5B

```
601  CAGGTGAGACTTTGGATGAAGCCCACAGACTGATATCTCAATGGTCAAGATCATTTAGTGATATTCGAGAAAGTACATGGATTCAGACAGCTTCGA   700
     hrGlyGluThrLeuAspGluSerProGlnThrAspIleSerMetValGlnAspHisPheSerAspIleArgArgLysTyrMetAspSerAspPheAs
      G  E  T  L  D  E  S  P  Q  T  D  I  S  M  V  Q  D  H  F  S  D  I  R  R  K  Y  M  D  S  D  F  D

701  TAGGCAGGCTTTAATAGCAAACAATACAATTAAGGCTTATTATGTCCGAAACTCCGCAGAAGCAGCATTGAAGTCGATCGACTGACACCGCACAACCCTCTC   800
     pArgGlnAlaLeuIleAlaAsnAsnThrIleLysAlaTyrTyrValArgAsnSerAlaLysSerAlaAlaLeuGluValAspLeuThrProHisAsnProLeu
      R  Q  A  L  I  A  N  N  T  I  K  A  Y  Y  V  R  N  S  A  K  A  A  L  E  V  D  L  T  P  H  N  P  L

801  AAAGTTTGTGACAATAAATTGACCATTGCAGGATTTCCTGACAGGAAGCTGAGCTGAGACAACAGGCCCGCCCAGAACTATTCAAGTAGATCAAGTTGC   900
     LysValCysAspAsnLysLeuThrIleAlaGlyPheProAspArgGluGluAlaGluGluLeuArgGlnThrGlyProProArgThrIleGlnValP
      K  V  C  D  N  K  L  T  I  A  G  F  P  D  R  E  A  E  L  R  Q  T  G  P  P  R  T  I  Q  V  P

901  CACCACCCTCGAAATCAGTTCATCACGAAGGAAAAAGTCTTTGTCAAGGCATAGCATGAGAATTACAATGGCATAGCTCTCTGTTGCCATTTGAAAAACAC   1000
     roProProSerLysSerValHisHisGluGlyLysSerLeuCysGlnGlyMetArgAsnTyrAsnGlyIleAlaSerValValCysHisLeuLysAsnTh
      P  P  P  S  K  S  V  H  H  E  G  K  S  L  C  Q  G  M  R  N  Y  N  G  I  A  S  V  V  C  H  L  K  N  T

1001 ATCAGGAAAGGAAAGAGCTTGTTGTTTGGAATTGGATATAATTCATTCATCATAACCGACATTTGTTCAAGGAGAATAATGGTGAACTTATAGTGAAA   1100
     rSerGlyLysGlyLysSerLeuPheGlyIleGlyTyrAsnSerPheIleIleThrAsnArgHisLeuPheLysGluAsnAsnGlyLeuIleValLys
      S  G  K  G  K  S  L  F  G  I  G  Y  N  S  F  I  I  T  N  R  H  L  F  K  E  N  N  G  E  L  I  V  K

1101 TCCCAACACGGTAAGTTTATTGTCAAGAACACCACAACACTCCGAATTGCTCCAGTTGGAAAGACTGATCTTTTAATTATTCGGATGCCGAAAGATTTC   1200
     SerGlnHisGlyLysPheIleValLysAsnThrThrLeuArgIleAlaProValGlyLysThrAspLeuLeuIleIleArgMetProLysAspPheP
      S  Q  H  G  K  F  I  V  K  N  T  T  L  R  I  A  P  V  G  K  T  D  L  L  I  I  R  M  P  K  D  F  P

1201 CTCCATTCCATAGCAGAGTCTAGGTTTAGGGCCATGAAAGCTGGGACAAGTTTGCATGATAGGTGTTGACTACCAAGAGAATCATATCGGAGCAAAGT   1300
     roPheHisSerArgAlaArgPheAlaMetLysAlaGlyAspLysValCysMetIleGlyValAspTyrGlnGluAsnHisIleAlaSerLysVa
      P  F  H  S  R  A  R  F  A  M  K  A  G  D  K  V  C  M  I  G  V  D  Y  Q  E  N  H  I  A  S  K  V
```

FIG. 5C

```
1301 ATCTGAAACCTCTATCATCAGTGAGGCACGGGAGATTTGGATGCCACTGATATCCACGAATGAGCGTGATTGCGGTAATCCTTAGTAGTGTTTCA  1400
     lSerGluThrSerIleIleSerGluGlyThrGlyAspPheGlyAspPheGlyCysHisTrpIleSerThrAsnAspGlyAspCysGlyAsnProLeuValSerValSer
     S  E  T  S  I  I  S  E  G  T  G  D  F  G  C  H  W  I  S  T  N  D  G  D  C  G  N  P  L  V  S  V  S

1401 GATGGTTTATTGTCGGCTTGCATAGTTGTCGACATCAACTGGAGATCAAAATTCTTTGCTAAAATACCCGCACAATTTGAAGAAAAGGTCCTTAGGA  1500
     AspGlyPheIleValGlyLeuHisSerLeuHisSerThrSerThrGlyAspGlnAsnPhePheAlaLysIleProAlaGlnPheGluGluLysValLeuArgL
     D  G  F  I  V  G  L  H  S  L  S  T  S  T  G  D  Q  N  F  F  A  K  I  P  A  Q  F  E  E  K  V  L  R  K

1501 AGATTGATGATTAACTTGGAGCAAACACTGGAGCTATAATATTAATGAACTGAGTTGGGAGCTCTCAAAGTGTGGAAAGTCGGCCCGAAGCAATTT  1600
     ysIleAspAspLeuThrTrpSerLysHisTrpSerTyrAsnIleAsnGluLeuSerTrpGlyAlaLeuLysValTrpGluSerArgProGluAlaIlePh
     I  D  D  L  T  W  S  K  H  W  S  Y  N  I  N  E  L  S  W  G  A  L  K  V  W  E  S  R  P  E  A  I  F

NcoI BamHI
                                        RMM334 <- - 3'  AAGCTCGTTGATCCAGATGGGTACCCTAGGCTGTTTAAT

1601 TAACGCGCAAAGGAAGTTAATCAATTGAATGTTTTCGAGCAAAGTGGTAGTCGTCGTTGGCTCTTTGACAAATTACACGGCCAATTTGAAAGGAGTTAGCTCC  1700
     eAsnAlaGlnLysGluValAsnGlnLeuAsnValPheGluGlnSerGlySerArgTrpLeuPheAspLysPheAspLysLeuHisGlyAsnLeuLysGlyValSerSer
     N  A  Q  K  E  V  N  Q  L  N  V  F  E  Q  S  G  S  R  W  L  F  D  K  L  H  G  N  L  K  G  V  S  S
                                           NIa|NIb                              NcoI      BamHI
                                 RMM355 <- - - 3'  CACACTACTTATCCGGTACCAAAGAACCTAGGTGAATACCC

1701 GCTCCTAGCAATTGGTGACAAAGCACGTTGTTAAAGGAATTTGTCCTCTTTTCAGGAACTATCTCGAGTGTGATGAATAGGCCCATGGTTGCGCTG  1797
     AlaProSerAsnLeuValThrLysHisValValLysGlyIleCysProLeuPheArgAsnTyrLeuGluCysAspGluEndAlaHisGlyCysAla
     A  P  S  N  L  V  T  K  H  V  V  K  G  I  C  P  L  F  R  N  Y  L  E  C  D  E  *  A  H  G  C  A
```

PAPAYA RINGSPOT VIRUS NIA PROTEASE GENE

CONTINUING APPLICATION INFORMATION

The present application is a continuation-in-part of U.S. Ser. No. 08/366,490, filed on Dec. 30, 1995, now U.S. Pat. No. 5,877,403.

FIELD OF THE INVENTION

This invention relates to a protease gene derived from papaya ringspot virus. More specifically, the invention relates to the genetic engineering of plants and to a method for conferring viral resistance to a plant using an expression cassette encoding papaya ringspot virus PRV FLA83 W or PRV USA P-type (HA attenuated) protease.

BACKGROUND OF THE INVENTION

Many agriculturally important crops are susceptible to infection by plant viruses, particularly papaya ringspot virus, which can seriously damage a crop, reduce its economic value to the grower, and increase its cost to the consumer. Attempts to control or prevent infection of a crop by a plant virus such as papaya ringspot virus have been made, yet viral pathogens continue to be a significant problem in agriculture.

Scientists have recently developed means to produce virus resistant plants using genetic engineering techniques. Such an approach is advantageous in that the genetic material which provides the protection is incorporated into the genome of the plant itself and can be passed on to its progeny. A host plant is resistant if it possesses the ability to suppress or retard the multiplication of a virus, or the development of pathogenic symptoms. "Resistant" is the opposite of "susceptible," and may be divided into: (1) high, (2) moderate, or (3) low resistance, depending upon its effectiveness. Essentially, a resistant plant shows reduced or no symptom expression, and virus multiplication within it is reduced or negligible. Several different types of host resistance to viruses are recognized. The host may be resistant to: (1) establishment of infection, (2) virus multiplication, or (3) viral movement.

Potyviruses are a distinct group of plant viruses which are pathogenic to various crops, and which demonstrate cross-infectivity between plant members of different families. Generally, a potyvirus is a single-stranded RNA virus that is surrounded by a repeating protein monomer, which is termed the coat protein (CP). The majority of the potyviruses are transmitted in a nonpersistent manner by aphids. As can be seen from the wide range of crops affected by potyviruses, the host range includes such diverse families of plants as Solanaceae, Chenopodiaceae, Gramineae, Compositae, Leguminosae, Dioscroeaceae, Cucurbitaceae, and Caricaceae. Potyviruses include watermelon mosaic virus II (WMVII), zucchini yellow mosaic virus (ZYMV), potato virus Y, tobacco etch and many others.

Another potyvirus of economic significance is papaya ringspot virus (PRV). Two groups of PRV have been identified: the "P" or "papaya ringspot" type infects papayas; and the "W" or "watermelon" type infects cucurbits, e.g., squash, but it is unable to infect papaya. Thus, these two groups can be distinguished by host range differences.

The potyviruses consist of flexous, filamentous particles of dimensions approximately 780×12 nanometers. The viral particles contain a single-stranded positive polarity RNA genome containing about 10,000 nucleotides. Translation of the RNA genome of potyviruses shows that the RNA encodes a single large polyprotein of about 330 kD. This polyprotein contains several proteins; these include the coat protein, nuclear inclusion proteins NIa and NIb, cytoplasmic inclusion protein (CI), and other proteases and movement proteins (see FIG. 1). These proteins are found in the infected plant cell and form the necessary components for viral replication. One of the proteins contained in the polyprotein is a 35 kD capsid or coat protein which coats and protects the viral RNA from degradation. One of the nuclear inclusion proteins, NIb, is an RNA replicase component and is thought to have polymerase activity. CI, a second inclusion protein, is believed to participate in the replicase complex and have a helicase activity. NIa, a third inclusion protein, has a protease activity. In the course of potyvirus infection, NIa and NIb are translationally transported across the nuclear membrane into the nucleus of the infected plant cell at the later stages of infection and accumulate to high levels.

The location of the protease gene appears to be conserved in these viruses. In the tobacco etch virus, the protease cleavage site has been determined to be the dipeptide Gln-Ser, Gln-Gly, or Gln-Ala.

Conservation of these dipeptides at the cleavage sites in these viral polyproteins is apparent from the sequences of the above-listed potyviruses.

Expression of the coat protein genes from tobacco mosaic virus, alfalfa mosaic virus, cucumber mosaic virus, and potato virus X, among others, in transgenic plants has resulted in plants which are resistant to infection by the respective virus. For reviews, see Fitchen et al., *Annu. Rev. Microbiol.*, 4, 739 (1993) and Wilson, *Proc. Natl. Acad. Sci. USA*, 90, 3134 (1993). For papaya ringspot virus, Ling et al. (*Bio/Technology*, 9, 752 (1991)) found that transgenic tobacco plants expressing the PRV coat protein (CP) gene isolated from the PRV strain HA 5-1 (mild) showed delayed symptom development and attenuation of symptoms after infection by a number of potyviruses, including tobacco etch (TEV), potato virus Y (PVY), and pepper mottle virus (PeMV). PRV does not infect tobacco, however. Thus, PRV CP transgenic tobacco plants cannot be used to evaluate protection against PRV. Fitch et al. (*Bio/Technology*, 10, 1466 (1992)), Gonsalves (*American J. of Bot.*, 79, 88 (1992)), and Lius et al. (91st *Annual Meeting of the American Society for Horticultural Science Hortscience*, 29, 483 (1994)) reported that four $R_0$ papaya plants made transgenic for a PRV coat protein gene taken from strain HA 5-1 (mild) displayed varying degrees of resistance against PRV infection, and one line (S55-1) appeared completely resistant to PRV. This appears to be the only papaya line that shows complete resistance to PRV infection.

Even though coat protein mediated viral resistance has proven to be useful in a variety of situations, it may not always be the most effective or desirable means for providing viral resistance. In such instances, it would be advantageous to have other methods for conferring viral resistance to plants. Expression of the protease gene (NIa) from tobacco vein mottle virus (TVMV) and potato virus Y (PVY) in transgenic plants has shown the feasibility of using protease gene constructs to produce transgenic plants protected against potyvirus infection (Maiti et al., *J. Cell. Biochem.*, Suppl. 16F, 217 (1992); Vardi et al., *Proc. Natl. Acad. Sci. U.S.A.*, 90, 7513 (1993); Maiti et al., *Proc. Natl. Acad. Sci. U.S.A.* 90, 6110 (1993)). Maiti et al. (1993) showed that the expression of the NIa gene of TVMV in tobacco plants rendered these plants highly resistant to TVMV challenge. In addition, Maiti et al. showed that the NIa gene expressed in these plants was proteolytically active. Vardi et al. transformed tobacco plants with PVY NIa constructs. $R_1$ progeny from two lines derived from these transformed plants were resistant to challenge with virus.

There is a continuing need for the transgenic expression of genes derived from potyviruses at levels which confer resistance to infection by these viruses.

SUMMARY OF THE INVENTION

This invention provides an isolated and purified DNA molecule that encodes the protease for the FLA83 W-type strain of papaya ringspot virus (PRV) or the protease for the PRV USA P-type (HA attenuated) strain. This invention also provides an isolated and purified DNA molecule that encodes the protease and flanking gene segments for the FLA83 W-type strain of papaya ringspot virus (PRV) or the protease and flanking gene segments for the PRV USA P-type (HA attenuated) strain. The invention also provides a chimeric expression cassette comprising at least one of these DNA molecules, a promoter which functions in plant cells to cause the production of an RNA molecule, and at least one polyadenylation signal comprising 3' nontranslated DNA which functions in plant cells to cause the termination of transcription and the addition of polyadenylated ribonucleotides to the 3' end of the transcribed mRNA sequences, wherein the promoter is operably linked to the DNA molecule, and the DNA molecule is operably linked to the polyadenylation signal. Another embodiment of the invention is exemplified by the insertion of multiple virus gene expression cassettes into one purified DNA molecule, e.g., a plasmid. Preferably, these cassettes include the promoter of the 35S gene of cauliflower mosaic virus and the polyadenylation signal of the cauliflower mosaic virus 35S gene.

Also provided are bacterial cells, and transformed plant cells, containing the chimeric expression cassettes comprising the protease gene derived from the FLA83 W-type strain of papaya ringspot virus (referred to herein as PRV FLA83 W) or from the USA P-type (HA attenuated) strain of PRV, and preferably the 35S promoter of cauliflower mosaic virus and the polyadenylation signal of the cauliflower mosaic virus 35S gene. Plants are also provided, wherein the plants comprise a plurality of transformed cells transformed with an expression cassette containing the protease gene derived from the PRV FLA83 W strain or from the USA P-type (HA attenuated) strain of PRV, and preferably the cauliflower mosaic virus 35S promoter and the polyadenylation signal of the cauliflower mosaic virus gene. Transformed plants of this invention include tobacco, corn, cucumber, peppers, potatoes, soybean, squash, and tomatoes. Especially preferred are members of the Cucurbitaceae (e.g., squash and cucumber) family.

Another aspect of the present invention is a method of preparing a PRV-resistant plant, such as a dicot, comprising: transforming plant cells with a chimeric expression cassette comprising a promoter functional in plant cells operably linked to a DNA molecule that encodes a protease as described above; regenerating the plant cells to provide a differentiated plant; and identifying a transformed plant that expresses the PRV protease at a level sufficient to render the plant resistant to infection by the specific strains of PRV disclosed herein.

As used herein, with respect to a DNA molecule or "gene," the phrase "isolated and purified" is defined to mean that the molecule is either extracted from its context in the viral genome by chemical means and purified and/or modified to the extent that it can be introduced into the present vectors in the appropriate orientation, i.e., sense or indecency. As used herein, the term "chimeric" refers to the linkage of two or more DNA molecules which are derived from different sources, strains or species (e.g., from bacteria and plants), or the linkage of two or more DNA molecules, which are derived from the same species and which are linked in a way that does not occur in the native genome. As used herein, the term "heterologous" is defined to mean not identical, e.g. different in nucleotide and/or amino acid sequence, phenotype or an independent isolate. As used herein, the term "expression" is defined to mean transcription or transcription followed by translation of a particular DNA molecule. As used herein, the term "flanking gene segments" means nucleotide sequences 5' to the proteolytically derived N-terminus of the NIa coding sequence and 3' to the proteolytically derived C-terminus of the NIa coding sequence, which include about 1000 nucleotides each.

BRIEF DESCRIPTION OF THE DRAWINGS

FIGS. 2A–2C. The nucleotide sequence of the nuclear inclusion body A (NIa) protease gene and flanking gene segments of PRV FLA83 W [SEQ ID NO:1]. The amino acid sequence of the encoded open reading frame is shown below the nucleotide sequence [SEQ ID NO:2. ]The nucleotide sequences of oligonucleotides RM354 [SEQ ID NO:3] and RMM355 [SEQ ID NO:4] are shown above the nucleotide sequence, at the 5' and 3' ends of the nucleotide sequence, respectively. The viral-specific sequences in RMM354 and RMM355 are homologous to sequences in PRV HA (attenuated) USA P (Quemada et al., *J. Gen. Virol.*, 71, 203 (1990)). In addition RMM354 has novel restriction endonuclease cleavage sites for EcoRI and NcoI while RMM355 has novel restriction endonuclease cleavage sites for BamHI and NcoI.

FIGS. 3A–3D. The alignment of the nucleotide sequences of the nuclear inclusion body A (NIa) and flanking gene segments from PRV isolates: HA-P (Yeh et al.,*J. Gen. Virol.,* 73, 2531 (1992)) [SEQ ID NO: 8]; USA P (Quemada et al., *J. Gen. Virol.,* 71, 203 (1990) [SEQ ID NO: 9; FLA83. Sequence alignments were generated using the UWGCG program Pileup. The dots represent either the lack of sequence information at the ends of the protease gene or gaps in homology in sequences relative to others in the alignment.

FIGS. 4A and 4B. The alignment of the amino acid sequences from papaya ringspot virus isolates described in FIG. 3 (USA-P-SEQ ID NO: 12 and HA-P-SEQ ID NO:13). Sequence differences between virus strains are underlined. The predicted cylindrical inclusion (CI)/VPg, VPg/NIa, and NIa/NIb cleavage sites are shown above the aligned amino acids (Q/G and Q/S). Alignments were generated using the UWGCG Pileup program. The dots represent either the lack of sequence information at the 5' end of the protease gene or gaps in homology in sequences relative to others in the alignment.

FIGS. 5A–5C. The nucleotide sequence of the nuclear inclusion body A (NIa) protease gene and flanking gene segments of PRV USA P-type strain [SEQ ID NO:5]. The amino acid sequence of the encoded open reading frame is shown below the nucleotide sequence [SEQ ID NO:6 and 7]. The nucleotide sequences of oligonucleotides RMM354 [SEQ ID NO:3] and RMM355 [SEQ ID NO:4] are shown at the 5' and 3' ends of the nucleotide sequence, respectively.

FIG. 6. A schematic representation of the cloning strategy for FLA83 gene expression cassettes.

FIGS. 8A and 8B. A schematic representation of the cloning strategy for PRV USA P-type (HA attenuated) gene expression cassettes with a stop codon near the 5' end of the coding sequences. Oligonucleotide primers RMM333 and RMM334 (see FIG. 5 for nucleotide sequence of these primers [SEQ ID NO:10 and 11, respectively]) were used to amplify PRV USA P-type (HA attenuated) NIa sequences and introduce a stop codon into the 5' portion of the NIa gene.

DETAILED DESCRIPTION OF THE INVENTION

Papaya ringspot virus (PRV) is a single-stranded (+) RNA plant virus that is translated into a single polyprotein. The viral RNA genome is approximately 10,000 bases in length. The expression strategy of potyviruses includes translation of a complete polyprotein from the positive sense viral genomic RNA. Translation of the genomic RNA produces a 330 kD protein which is subsequently cleaved into at least seven smaller viral proteins by a virally encoded protease. The virally encoded proteins include a 35 kD protein at the amino terminal end of the 330 kD protein which is thought to be involved in cell to cell transmission, H C protein is 56 kD in size and is believed to be involved in insect transmission and possess proteolytic activity, a 50 kD protein, a 90 kD cylindrical inclusion protein (CI), which is part of the replicase complex and possesses helicase activity, a 6 kD VPg protein which is covalently attached to the 5' end of the viral genomic RNA, a 49 kD NIa protein which functions as a protease, a 60 kD NIb protein which functions as a polymerase, and the coat protein (36 kD).

Two types of PRV have been established based on host range. One type is designated "P type"; it infects Caricacae (e.g., papaya), Cucurbitaceae (e.g., cucurbitis), and Chenopodiaceae (e.g., Chenopodium) (Wang et al., *Phytopathology,* 84, 1205 (1994)). A second type is designated "W type"; it infects only Cucurbitaceae and Chenopodiaceae (Wang et al., *Phytopathology,* 84, 1205 (1994)). Isolates of the P type include HA-severe, called HA-P herein (Wang et al., *Phytopath.,* 127, 349 (1992)), HA5-1, called USA P herein, YK (Wang et al., *Phytopathology,* 84, 1205 (1994)), and other isolates as described in Tennant et al. (*Phytopathology,* 84, 1359 (1994)). Isolates of the W type include FLA83, disclosed herein, PRV-W type (Yeh et al., *Phytopathology,* 74, 1081 (1984)) and PRV-W (Aust) (Bateson et al., *Arch-Viol.,* 123, 101 (1992)).

To practice the present invention, the protease (NIa) gene of a virus must be isolated from the viral genome and inserted into a vector. Thus, the present invention provides isolated and purified DNA molecules that encode either an NIa protease of PRV FLA83 or an NIa protease of PRV USA P-type (HA attenuated). As used herein, a DNA molecule that encodes a protease gene includes nucleotides of the coding strand, also referred to as the "sense" strand, as well as nucleotides of the noncoding strand, complementary strand, also referred to as the "antisense" strand, either alone or in their base-paired configuration. For example, a DNA molecule that encodes the protease of PRV FLA83, for example, includes the DNA molecule having the nucleotide sequence of FIGS. 2A–2C [SEQ ID NO:1], a DNA molecule complementary to the nucleotide sequence of FIGS. 2A–2C [SEQ ID NO:1], as well as a DNA molecule which also encodes a PRV FLA83 NIa protease and its complement which hybridizes with a PRV FLA83-specific DNA probe in hybridization buffer with 6×SSC, 5× Denhardt's reagent, 0.5% SDS and 100 μg/ml denatured, fragmented salmon sperm DNA and remains bound when washed at 68° C. in 0.1×SSC and 0.5% SDS (Sambrook et al., *Molecular Cloning: A Laboratory Manual,* 2nd ed. (1989)). Moreover, the DNA molecules of the present invention can include non-PRV NIa protease nucleotides that do not interfere with expression, such as the nucleotide sequences in the flanking gene segments.

The PRV protease gene does not contain the signals necessary for its expression once transferred and integrated into a plant genome. Accordingly, a vector must be constructed to provide the regulatory sequences such that they will be functional upon inserting a desired gene. When the expression vector/insert construct is assembled, it is used to transform plant cells which are then used to regenerate plants. These transgenic plants carry the viral gene in the expression vector/insert construct. The gene is expressed in the plant and increased resistance to viral infection is conferred thereby.

Several different methods exist to isolate the protease gene. To do so, one having ordinary skill in the art can use information about the genomic organization of potyviruses to locate and isolate the protease gene. The protease gene is located in the 3' half of the genome, between the VPg gene and the NIb gene (FIG. 1). Additionally, the information related to proteolytic cleavage sites is used to determine the N-terminus of the protease gene. The protease recognition sites are conserved in the potyviruses and have been determined to be either the dipeptide Gln-Ser, Gln-Gly, or Gln-Ala. The nucleotide sequences which encode these dipeptides can be determined.

Using methods well known in the art, a quantity of virus is grown and harvested. The viral RNA is then separated and the protease gene isolated using a number of known procedures. A cDNA library is created using the viral RNA, by methods known to the art. The viral RNA is incubated with primers that hybridize to the viral RNA and reverse transcriptase, and a complementary DNA molecule is produced. A DNA complement of the complementary DNA molecule is produced and that sequence represents a DNA copy (cDNA) of the original viral RNA molecule. The DNA complement can be produced in a manner that results in a single double stranded cDNA or polymerase chain reactions can be used to amplify the DNA encoding the cDNA with the use of oligomer primers specific for the protease gene. These primers can include novel restriction sites used in subsequent cloning steps. Thus, a double stranded DNA molecule is generated which contains the sequence information of the viral RNA. These DNA molecules can be cloned in *E. coli* plasmid vectors after the additions of restriction enzyme linker molecules by DNA ligase. The various fragments are inserted into cloning vectors, such as well-characterized plasmids, which are then used to transform *E. coli* and create a cDNA library.

Previously identified PRV NIa genes can be used as hybridization probes to screen the cDNA library to determine if any of the transformed bacteria contain DNA fragments with sequences coding for the protease region. The cDNA inserts in any bacterial colonies which contain this region can be sequenced. The protease gene is present in its entirety in colonies which have sequences that extend 5' to sequences which encode a N-terminal proteolytic cleavage site and 3' to sequences which encode a C-terminal proteolytic cleavage site for NIa.

Alternatively, cDNA fragments can be inserted in the sense orientation into expression vectors. Antibodies against the protease can be used to screen the cDNA expression library and the gene can be isolated from colonies which express the protein.

Figure 1:
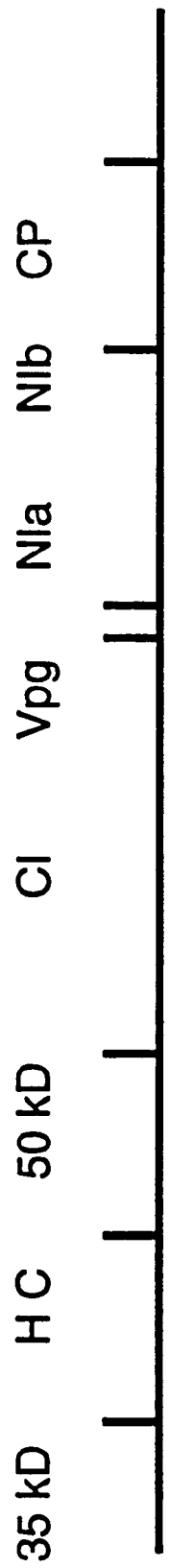
FIG. 1. Schematic representation of the genomic organization of potyviruses.

Another molecular strategy to provide virus resistance in transgenic plants is based on antisense RNA. As is well known, a cell manufactures protein by transcribing the DNA of the gene encoding that protein to produce RNA, which is then processed to messenger RNA (mRNA) (e.g., by the removal of introns) and finally translated by ribosomes into protein. This process may be inhibited in the cell by the presence of antisense RNA. The term antisense RNA means an RNA sequence which is complementary to a sequence of bases in the mRNA in question in the sense that each base (or the majority of bases) in the antisense sequence (read in the 3' to 5' sense) is capable of pairing with the corresponding base (G with C, A with U) in the mRNA sequence read in the 5' to 3' sense. It is believed that this inhibition takes place by formation of a complex between the two complementary strands of RNA, thus preventing the formation of protein. How this works is uncertain: the complex may interfere with further transcription, processing, transport or translation, or degrade the mRNA, or have more than one of these effects. This antisense RNA may be produced in the cell by transformation of the cell with an appropriate DNA construct arranged to transcribe the non-template strand (as opposed to the template strand) of the relevant gene (or of a DNA sequence showing substantial homology therewith).

The use of antisense RNA to downregulate the expression of specific plant genes is well known. Reduction of gene expression has led to a change in the phenotype of the plant: either at the level of gross visible phenotypic difference, e.g., lack of anthocyanin production in flower petals of petunia leading to colorless instead of colored petals (van der Krol et al., *Nature,* 333:866–869 (1988)); or at a more subtle biochemical level, e.g., change in the amount of polygalacturonase and reduction in depolymerization of pectin during tomato fruit ripening (Smith et al., *Nature,* 334:724–726 (1988)).

Another more recently described method of inhibiting gene expression in transgenic plants is the use of sense RNA transcribed from an exogenous template to downregulate the expression of specific plant genes (Jorgensen, Keystone Symposium "Improved Crop and Plant Products through Biotechnology," Abstract X1-022 (1994)). Thus, both antisense and sense RNA have been proven to be useful in achieving downregulation of gene expression in plants.

In the present invention, the DNA molecules encoding the protease genes of PRV FLA83 W strain and the USA P-Type (HA attenuated) strain have been determined and the genes have been inserted into expression vectors. These expression cassettes can be individually placed into a vector that can be transmitted into plants, preferably a binary vector. Alternatively, two or more of the PRV protease genes can each be present in an expression cassette which can be placed into the same binary vector, or any one of the PRV NIa expression cassettes of the present invention can be placed into a binary vector with one or more viral gene expression cassettes. The expression vectors contain the necessary genetic regulatory sequences for expression of an inserted gene. The protease gene is inserted such that those regulatory sequences are functional and the genes can be expressed when incorporated into a plant genome. For example, vectors of the present invention can contain combinations of expression cassettes that include DNA from a papaya ringspot virus (PRV) coat protein gene or a heterologous PRV protease gene (e.g., one that is from a different strain), a cucumber mosaic virus coat protein gene, a zucchini yellow mosaic virus coat protein gene, and a watermelon mosaic virus-2 coat protein gene.

Moreover, when combinations of viral gene expression cassettes are placed in the same binary plasmid, and that multigene cassette containing plasmid is transformed into a plant, the multiple viral genes all preferably exhibit substantially the same degrees of efficacy when present in transgenic plants. For example, if one examines numerous transgenic lines containing two different intact viral gene expression cassettes, the transgenic line will be immune to infection by both viruses. Similarly, if a line exhibits a delay in symptom development to one virus, it will also exhibit a delay in symptom development to the second virus. Finally, if a line is susceptible to one of the viruses it will be susceptible to the other. This phenomenon is unexpected. If there were not a correlation between the performance of each gene in these multiple gene constructs, this approach as a tool in plant breeding would probably be prohibitively difficult to use. Even with single gene constructs, one must test numerous transgenic plant lines to find one that displays the appropriate level of efficacy. The probability of finding a line with useful levels of expression can range from 10–50% (depending on the species involved). For further information refer to Applicants' Assignees copending patent application Ser. No. 08/366,991 entitled "Transgenic Plants Expressing DNA Constructs Containing a Plurality of Genes to Impart Virus Resistance" filed on Dec. 30, 1994, incorporated by reference herein.

In order to express the viral gene, the necessary genetic regulatory sequences must be provided. Since the protease of a potyvirus is produced by the post-translational processing of a polyprotein the protease gene isolated from viral RNA does not contain transcription and translation signals necessary for its expression once transferred and integrated into a plant genome. It must, therefore, be engineered to contain a plant expressible promoter, a translation initiation codon (ATG), and a plant functional poly(A) addition signal (AATAAA) 3' of its translation termination codon. In the present invention, the protease genes are inserted into vectors which contain cloning sites for insertion 3' of the initiation codon and 5' of the poly(A) signal. The promoter is 5' of the initiation codon such that when structural genes are inserted at the cloning site, a functional unit is formed in which the inserted genes are expressed under the control of the various genetic regulatory sequences.

The segment of DNA referred to as the promoter is responsible for the regulation of the transcription of DNA into mRNA. A number of promoters which function in plant cells are known in the art and can be employed in the practice of the present invention. These promoters can be obtained from a variety of sources such as plants or plant viruses, and can include, but are not limited to, promoters isolated from the caulimovirus group such as the cauliflower mosaic virus 35S promoter (CaMV35S), the enhanced cauliflower mosaic virus 35S promoter (enh CaMV35S), the figwort mosaic virus full-length transcript promoter (FMV35S), and the promoter isolated from the chlorophyll a/b binding protein. Other useful promoters include promoters which are capable of expressing the potyvirus proteins in an inducible manner or in a tissue-specific manner in certain cell types in which the infection is known to occur. For example, the inducible promoters from phenylalanine ammonia lyase, chalcone synthase, hydroxyproline rich glycoprotein, extension, pathogenesis-related proteins (e.g. PR-1a), and wound-inducible protease inhibitor from potato may be useful.

Preferred promoters for use in the present protease-containing cassettes include the constitutive promoters from CaMV, the Ti genes nopaline synthase (Bevan et al., *Nucleic Acids Res. II,* 369 (1983)) and octopine synthase (Depicker et al., *J. Mol. Appl. Genet.,* 1, 561 (1982)), and the bean storage protein gene phaseolin. The poly(A) addition signals from these genes are also suitable for use in the present cassettes. The particular promoter selected is preferably capable of causing sufficient expression of the DNA coding sequences to which it is operably linked, to result in the production of amounts of the proteins or RNAs effective to provide viral resistance, but not so much as to be detrimental to the cell in which they are expressed. The promoters selected should be capable of functioning in tissues including, but not limited to, epidermal, vascular, and mesophyll tissues. The actual choice of the promoter is not critical, as long as it has sufficient transcriptional activity to accomplish the expression of the preselected proteins or sense and/or antisense RNAs and subsequent conferral of viral resistance to the plants.

The nontranslated leader sequence can be derived from any suitable source and can be specifically modified to increase the translation of the mRNA. The 5' nontranslated region can be obtained from the promoter selected to express the gene, an unrelated promoter, the native leader sequence of the gene or coding region to be expressed, viral RNAs, suitable eucaryotic genes, or a synthetic gene sequence. The present invention is not limited to the constructs presented in the following examples.

The termination region or 3' nontranslated region which is employed is one which will cause the termination of transcription and the addition of polyadenylated ribonucleotides to the 3' end of the transcribed mRNA sequence. The termination region can be native with the promoter region, native with the structural gene, or can be derived from another source, and preferably include a terminator and a sequence coding for polyadenylation. Suitable 3' nontranslated regions of the chimeric plant gene include but are not limited to: (1) the 3' transcribed, nontranslated regions containing the polyadenylation signal of Agrobacterium tumor-inducing (Ti) plasmid genes, such as the nopaline synthase (NOS) gene; and (2) plant genes like the soybean 7S storage protein genes.

Preferably, the expression cassettes of the present invention are engineered to contain a constitutive promoter 5' to its translation initiation codon (ATG) and a poly(A) addition signal (AATAAA) 3' to its translation termination codon. Several promoters which function in plants are available, however, the preferred promoter is the 35S constitutive promoters from cauliflower mosaic virus (CaMV). The poly(A) signal can be obtained from the CaMV 35S gene or from any number of well characterized plant genes, i.e., nopaline synthase, octopine synthase, and the bean storage protein gene phaseolin. The constructions are similar to that used for the expression of the CMV C coat protein in PCT Patent Application PCT/US88/04321, published on Jun. 29, 1989 as WO 89/05858, claiming the benefit of U.S.S.N. 135,591, filed Dec. 21, 1987, entitled "Cucumber Mosaic Virus Coat Protein Gene," and the CMV WL coat protein in PCT Patent Application PCT/US89/03288, published on Mar. 8, 1990 as WO 90/02185, claiming the benefit of U.S.S.N. 234,404, filed Aug. 19, 1988, entitled "Cucumber Mosaic Virus Coat Protein Gene."

Selectable marker genes can be incorporated into the present expression cassettes and used to select for those cells or plants which have become transformed. The marker gene employed may express resistance to an antibiotic, such as kanamycin, gentamycin, G418, hygromycin, streptomycin, spectinomycin, tetracycline, chloramphenicol, and the like. Other markers could be employed in addition to or in the alternative, such as, for example, a gene coding for herbicide tolerance such as tolerance to glyphosate, sulfonylurea, phosphinothricin, or bromoxynil. Additional means of selection could include resistance to methotrexate, heavy metals, complementation providing prototropy to an auxotrophic host, and the like.

The particular marker employed will be one which will allow for the selection of transformed cells as opposed to those cells which are not transformed. Depending on the number of different host species one or more markers can be employed, where different conditions of selection would be useful to select the different host, and would be known to those of skill in the art. A screenable marker such as the β-glucuronidase gene can be used in place of, or with, a selectable marker. Cells transformed with this gene can be identified by the production of a blue product on treatment with 5-bromo-4-chloro-3-indoyl-β-D-glucuronide (X-Gluc).

In developing the present expression construct, i.e., expression cassette, the various components of the expression construct such as the DNA molecules, linkers, or fragments thereof will normally be inserted into a convenient cloning vector, such as a plasmid or phage, which is capable of replication in a bacterial host, such as *E. coli*. Numerous cloning vectors exist that have been described in the literature. After each cloning, the cloning vector can be isolated and subjected to further manipulation, such as restriction, insertion of new fragments, ligation, deletion, resection, insertion, in vitro mutagenesis, addition of polylinker fragments, and the like, in order to provide a vector which will meet a particular need.

For Agrobacterium-mediated transformation, the expression cassette will be included in a vector, and flanked by fragments of the Agrobacterium Ti or Ri plasmid, representing the right and, optionally the left, borders of the Ti or Ri plasmid transferred DNA (T-DNA). This facilitates integration of the present chimeric DNA sequences into the genome of the host plant cell. This vector will also contain sequences that facilitate replication of the plasmid in Agrobacterium cells, as well as in *E. coli* cells.

All DNA manipulations are typically carried out in *E. coli* cells, and the final plasmid bearing the potyvirus gene expression cassette is moved into Agrobacterium cells by direct DNA transformation, conjugation, and the like. These Agrobacterium cells will contain a second plasmid, also derived from Ti or Ri plasmids. This second plasmid will carry all the viral genes required for transfer of the foreign DNA into plant cells. Suitable plant transformation cloning vectors include those derived from a Ti plasmid of *Agrobacterium tumefaciens*, as generally disclosed in Glassman et al. (U.S. Pat. No. 5,258,300), or *Agrobacterium rhizogenes*.

A variety of techniques are available for the introduction of the genetic material into or transformation of the plant cell host. However, the particular manner of introduction of the plant vector into the host is not critical to the practice of the present invention, and any method which provides for efficient transformation can be employed. In addition to transformation using plant transformation vectors derived from the tumor-inducing (Ti) or root-inducing (Ri) plasmids of Agrobacterium, alternative methods could be used to insert the DNA constructs of the present invention into plant cells. Such methods may include, for example, the use of liposomes, electroporation, chemicals that increase the free uptake of DNA (Paszkowski et al., *EMBO J.,* 3, 2717

(1984)), microinjection (Crossway et al., *Mol. Gen. Genet.,* 202, 179 (1985)), electroporation (Fromm et al., *Proc. Natl. Acad. Sci. USA,* 2, 824 (1985)), or high-velocity microprojectiles (Klein et al., *Nature,* 327, 70 (1987) and transformation using viruses or pollen.

The choice of plant tissue source or cultured plant cells for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is regenerable, in that it will retain the ability to regenerate whole, fertile plants following transformation The transformation is carried out under conditions directed to the plant tissue of choice. The plant cells or tissue are exposed to the DNA carrying the present potyvirus multi-gene expression cassette for an effective period of time. This can range from a less-than-one-second pulse of electricity for electroporation, to a two-to-three day co-cultivation in the presence of plasmid-bearing Agrobacterium cells. Buffers and media used will also vary with the plant tissue source and transformation protocol. Many transformation protocols employ a feeder layer of suspended culture cells (tobacco or Black Mexican Sweet Corn, for example) on the surface of solid media plates, separated by a sterile filter paper disk from the plant cells or tissues being transformed.

Following treatment with DNA, the plant cells or tissue may be cultivated for varying lengths of time prior to selection, or may be immediately exposed to a selective agent such as those described hereinabove. Protocols involving exposure to Agrobacterium will also include an agent inhibitory to the growth of the Agrobacterium cells. Commonly used compounds are antibiotics such as cefotaxime and carbenicillin. The media used in the selection may be formulated to maintain transformed callus or suspension culture cells in an undifferentiated state, or to allow production of shoots from callus, leaf or stem segments, tuber disks, and the like.

Cells or callus observed to be growing in the presence of normally inhibitory concentrations of the selective agents are presumed to be transformed and may be subcultured several additional times on the same medium to remove nonresistant sections. The cells or callus can then be assayed for the presence of the viral gene cassette, or can be subjected to known plant regeneration protocols. In protocols involving the direct production of shoots, those shoots appearing on the selective media are presumed to be transformed and can be excised and rooted, either on selective medium suitable for the production of roots, or by simply dipping the excised shoot in a root-inducing compound and directly planting it in vermiculite.

In order to produce transgenic plants exhibiting viral resistance, the viral genes must be taken up into the plant cell and stably integrated within the plant genome. Plant cells and tissues selected for their resistance to an inhibitory agent are presumed to have acquired the selectable marker gene encoding this resistance during the transformation treatment. Since the marker gene is commonly linked to the viral genes, it can be assumed that the viral genes have similarly been acquired. Southern blot hybridization analysis using a probe specific to the viral genes can then be used to confirm that the foreign genes have been taken up and integrated into the genome of the plant cell. This technique may also give some indication of the number of copies of the gene that have been incorporated. Successful transcription of the foreign gene into mRNA can likewise be assayed using Northern blot hybridization analysis of total cellular RNA and/or cellular RNA that has been enriched in a polyadenylated region. mRNA molecules encompassed within the scope of the invention are those which contain viral specific sequences derived from the viral genes present in the transformed vector which are of the same polarity as that of the viral genomic RNA such that they are capable of base pairing with viral specific RNA of the opposite polarity to that of viral genomic RNA under conditions described in Chapter 7 of Sambrook et al. (1989). Moreover, mRNA molecules encompassed within the scope of the invention are those which contain viral specific sequences derived from the viral genes present in the transformed vector which are of the opposite polarity to that of the viral genomic RNA such that they are capable of base pairing with viral genomic RNA under conditions described in Chapter 7 in Sambrook et al. (1989).

The presence of a viral protease gene can also be detected by indirect assays, such as the Western blot assay described by Maiti et al. (*Proc. Natl. Acad. Sci. U.S.A.* 90, 6110 (1993)). Maiti et al. constructed a fusion protein containing the TVMV NIa protease and the *E. coli* glnH gene and transformed the construct into tobacco. Transgenic plants were assayed by Western blot analysis for the glnH gene product with an antibody to glnH. Not only was a glnH protein expressed in these plants, the glnH product was cleaved out of the fusion protein, presumably by NIa.

Potyvirus resistance can also be assayed via infectivity studies as generally disclosed by Namba et al. (*Gene,* 107, 181 (1991)) wherein plants are scored as symptomatic when any inoculated leaf shows veinclearing, mosaic or necrotic symptoms.

Seed from plants regenerated from tissue culture is grown in the field and self-pollinated to generate true breeding plants. The progeny from these plants become true breeding lines which are evaluated for viral resistance in the field under a range of environmental conditions. The commercial value of viral-resistant plants is greatest if many different hybrid combinations with resistance are available for sale. Additionally, hybrids adapted to one part of a country are not adapted to another part because of differences in such traits as maturity, disease and insect tolerance. Because of this, it is necessary to breed viral resistance into a large number of parental lines so that many hybrid combinations can be produced.

Adding viral resistance to agronomically elite lines is most efficiently accomplished when the genetic control of viral resistance is understood. This requires crossing resistant and sensitive plants and studying the pattern of inheritance in segregating generations to ascertain whether the trait is expressed as dominant or recessive, the number of genes involved, and any possible interaction between genes if more than one is required for expression. With respect to transgenic plants of the type disclosed herein, the transgenes exhibit dominant, single gene Mendelian behavior. This genetic analysis can be part of the initial efforts to convert agronomically elite, yet sensitive lines to resistant lines. A conversion process (backcrossing) is carried out by crossing the original transgenic resistant line with a sensitive elite line and crossing the progeny back to the sensitive parent. The progeny from this cross will segregate such that some plants carry the resistance gene(s) whereas some do not. Plants carrying the resistance gene(s) will be crossed again to the sensitive parent resulting in progeny which segregate for resistance and sensitivity once more. This is repeated until the original sensitive parent has been converted to a resistant line, yet possesses all of the other important attributes originally found in the sensitive parent. A separate backcrossing program is implemented for every sensitive elite line that is to be converted to a virus resistant line.

Subsequent to the backcrossing, the new resistant lines and the appropriate combinations of lines which make good commercial hybrids are evaluated for viral resistance, as well as for a battery of important agronomic traits. Resistant lines and hybrids are produced which are true to type of the original sensitive lines and hybrids. This requires evaluation under a range of environmental conditions under which the lines or hybrids will be grown commercially. Parental lines of hybrids that perform satisfactorily are increased and utilized for hybrid production using standard hybrid production practices.

The invention will be further described by reference to the following detailed examples. Enzymes were obtained from commercial sources and were used according to the vendor's recommendations or other variations known in the art. Other reagents, buffers, etc., were obtained from commercial sources, such as GIBCO-BRL, Bethesda, Md., and Sigma Chemical Co., St. Louis, Mo., unless otherwise specified.

Most of the recombinant DNA methods employed in practicing the present invention are standard procedures, well known to those skilled in the art, and described in detail in, for example, European Patent Application Publication Number 223,452, published Nov. 29, 1986, which is incorporated herein by reference. General references containing such standard techniques include the following: R. Wu, ed., *Methods in Enzymology*, Vol. 68 (1979); J. H. Miller, *Experiments in Molecular Genetics* (1972); J. Sambrook et al., *Molecular Cloning: A Laboratory Manual*, 2nd ed. (1989); and D. M. Glover, ed., *DNA Cloning Vol. II* (1982).

Figure 6:
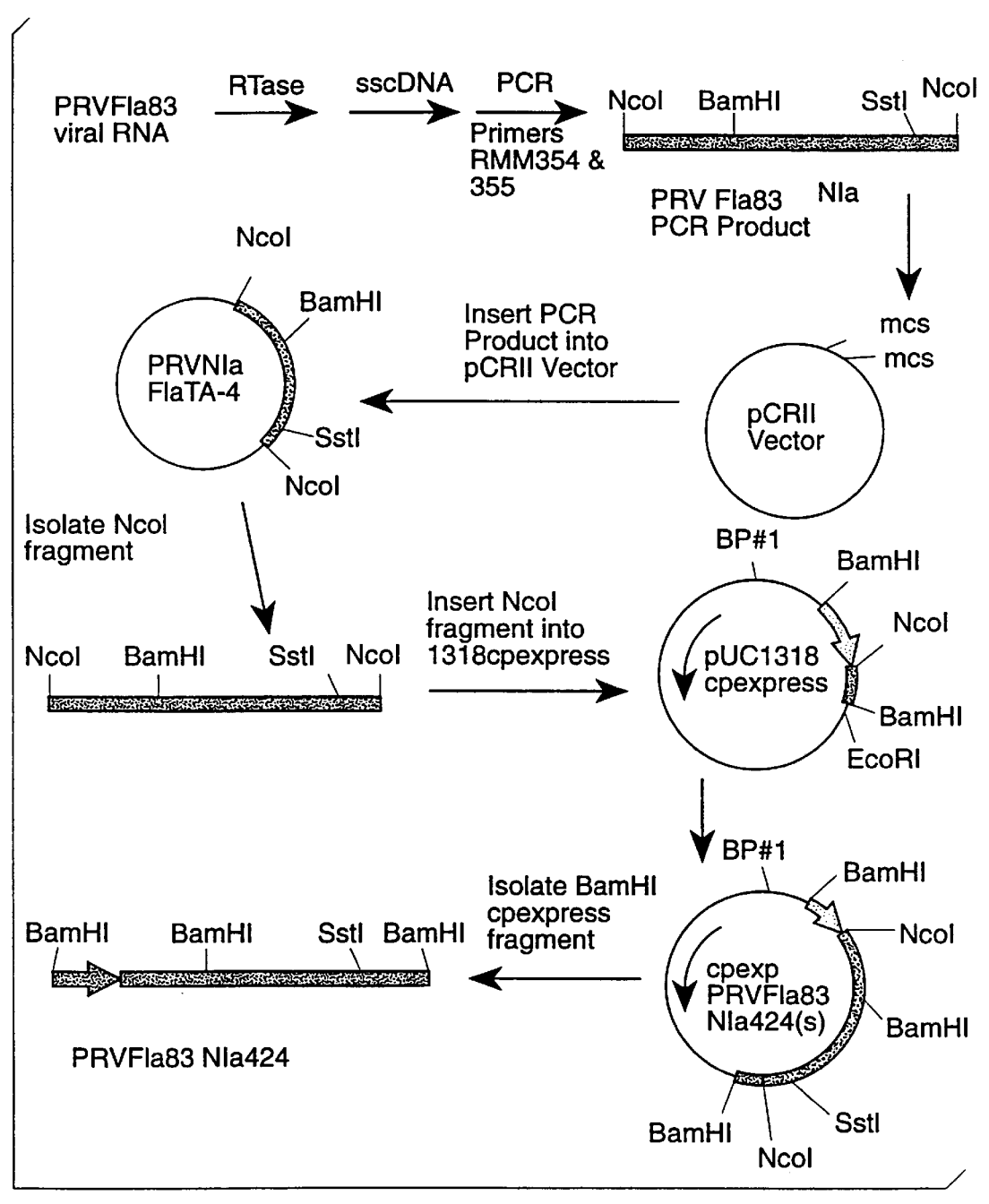

FIGS. 6–8 are presented to illustrate the constructions of this invention.

EXAMPLE I

To isolate and engineer the PRV NIa gene, the following steps can be used: 1) Purify PRV virions and isolate PRV viral RNA from the virion preparation; 2) construct single-stranded cDNAs of PRV viral RNA; 3) amplify NIa sequences by PCR amplification using viral sequence specific primers; 4) clone the PCR product into a plant expression cassette placed into an appropriate binary vector; 5) produce PRV NIa transgenic plants; and 6) challenge the progeny of $R_0$ transgenic plants to identify lines which confer the desired properties.

A. Isolation of PRV FLA83-W Viral RNA

Papaya Ringspot virus FLA83 W-type was deposited with American Type Culture Collection (ATCC), 10801 University Blvd., Manassas, Va. on Aug. 3, 1998 and assigned ATCC Deposit Number 203076. Papaya Ringspot virus USA P-type (also known as HA 5-1) was deposited with the Deutsche Sammlung von Mikroorganismen und Zellkulturen GmbH, Maacheroder Weg 1b, D-38124 Braunschweig, Germany on Sep. 28, 1998 and assigned DSM Accession Number 12454. These deposits were made in compliance with the requirements of the Budapest Treaty that the duration of the deposits should be for thirty (30) years from the date of deposit or for five (5) years after the last request for the deposit at the depositories or for the enforceable life of a U.S. Patent that matures from this application, whichever is longer. Plant virus strains of FLA 83 W-type and USA P-type (HA-5) will be replenshied should either of these viruses become non-viable at either depository.

7-day-old yellow crookneck squash plants grown in the greenhouse were inoculated with PRV strain W (watermelon) Florida-83; 21 days post inoculation leaves were harvested and PRV virus isolated. The procedure used was based on a modified method used by Purcifull et al. (*Phytopathology*, 69, 112 (1979)) for PRV type W isolation. Approximately 50 grams of fresh leaf tissue was homogenized in 100 ml 0.5 M potassium phosphate buffer (pH 7.5 "PB") containing 0.1% sodium sulphate, 25 ml chloroform, and 25 ml carbon tetrachloride. After centrifugation of the extract at 1,000×g for 5 minutes the pellet was resuspended in 50 ml of PB buffer and centrifuged again at 1,000×g for 5 minutes. The supernatants from each centrifugation are pooled then centrifuged at 13,000×g for 15 minutes. To the resulting supernatant, Triton X-100 was added to a final concentration of 1% (v/v), polyethyleneglycol (PEG) 8,000 (Reagent grade from Sigma Chemical Co.) to a final concentration of 4% (w/v) and NaCl to a final concentration of 100 mM. The suspension was stirred for 1 hour at 0–40 C. This suspension was centrifuged at 10,000×g for 10 minutes.

The pellet was resuspended in 40 ml of PB. After centrifugation at 12,000×g for 10 minutes the pellet was discarded and virus was precipitated from the supernatant by adding PEG to a final concentration of 8% (w/v) and NaCl to a final concentration of 100 mM, and stirring for 0.5 hour at 0–4° C. After centrifugation at 12,000×g for 10 minutes the pellets were resuspended with the aid of a tissue grinder in 5 ml of 20 mM PB and layered over a 30% $Cs_2SO_4$ cushion.

This suspension was centrifuged in a Beckman Ti75 at 140,000×g for 18 hours at 5° C. After centrifugation, the virus band was harvested and dialyzed against 20 mM PB overnight at 4° C. The dialyzed virus preparation was lysed and viral RNA precipitated by the addition of LiCl to a final concentration of 2M. The viral RNA was recovered by centrifugation. Viral RNA was dissolved and precipitated by ethanol and resuspended in water.

B. Cloning and Engineering PRV Protease Genes (a) FLA83 W

PRV FLA83 W RNA was prepared as described above. Subsequently, the first cDNA strand was synthesized using PRV FLA83 W RNA template in a reaction that included the following: approximately 3–5 µg PRV FLA83 W RNA, 1×buffer for Superscript Reverse Transcriptase (supplied by BRL-GIBCO, Grand Island, N.Y.), 2 mM dNTPs, oligomer primer RMM355 (37.5 µg/mL, SEQ ID NO:4), 2.0 µL RNasin (Promega, Madison, Wis.), and 2.5 µL Superscript Reverse Transcriptase (BRL-GIBCO) in a 20-µL reaction. After this reaction was allowed to proceed for 30 minutes at 37° C., an aliquot of the first strand reaction was used as a template in a polymerase chain reaction with RMM354 and RMM355 [SEQ ID NO: 3 and 4, respectively] to amplify a region of the FLA83 W genome (FIG. 6). The RM354 primer supplies an ATG translation initiation codon. This region includes 189 base pairs of the 3' end of the CI gene, the entire VPg gene, the entire NIa protease gene, and 146 base pairs of the 5' end of the NIb gene. The 1835 bp PCR amplified product was cloned into the pCRII vector included in the TA Cloning™ Kit supplied by Invitrogen Corp. A clone was recovered that contained PRV sequences (PRVNIaFLA TA-4). This clone was sequenced with the use of a kit (Sequenase 2 purchased from USB, Cleveland, Ohio).

The 1789 bp NcoI fragment of PRVNIaFLA TA-4 containing PRV sequences was excised from PRVNIaFLA TA-4, isolated and inserted into the plant expression cassette pUC1318cpexpress. Cassettes containing the insert of PRV sequences in the sense orientation were isolated by a partial BamHI digestion (PRVFla83 NIa424) and inserted into the BglII site of pEPG111 to give pEPG250 (for further information on parental binary vectors shown in Table 1, see Applicants' Assignees copending patent application Ser. No. 08/366,991 entitled "Transgenic Plants Expressing DNA Constructs Containing a Plurality of Genes to Impart Virus Resistance" filed on Dec. 30, 1994, incorporated by reference herein. For further information on PRV coat protein genes, see Applicants' Assignees copending patent application Ser. No. 08/366,881 entitled "Papaya Ringspot Virus Coat Protein Gene" filed on Dec. 30, 1994, incorporated by reference herein. For further information on ZYMV and WMV2 coat protein genes, see Applicants' Assignees copending patent application Ser. No. 08/232,846 filed on Apr. 25, 1994 entitled "Potyvirus Coat Protein Genes and Plants Transformed Therewith," incorporated by reference herein. For further information on CMV-C and CMV-wl coat protein genes, see Quemada et al., *J. Gen. Virol.*, 70, 1065 (1989). The binary plasmids were transformed into *Agrobacterium tumefaciens* strain C58Z707 and Mog301 (Table 1)

(b) USA Type P (HA attenuated)

Figure 7A:
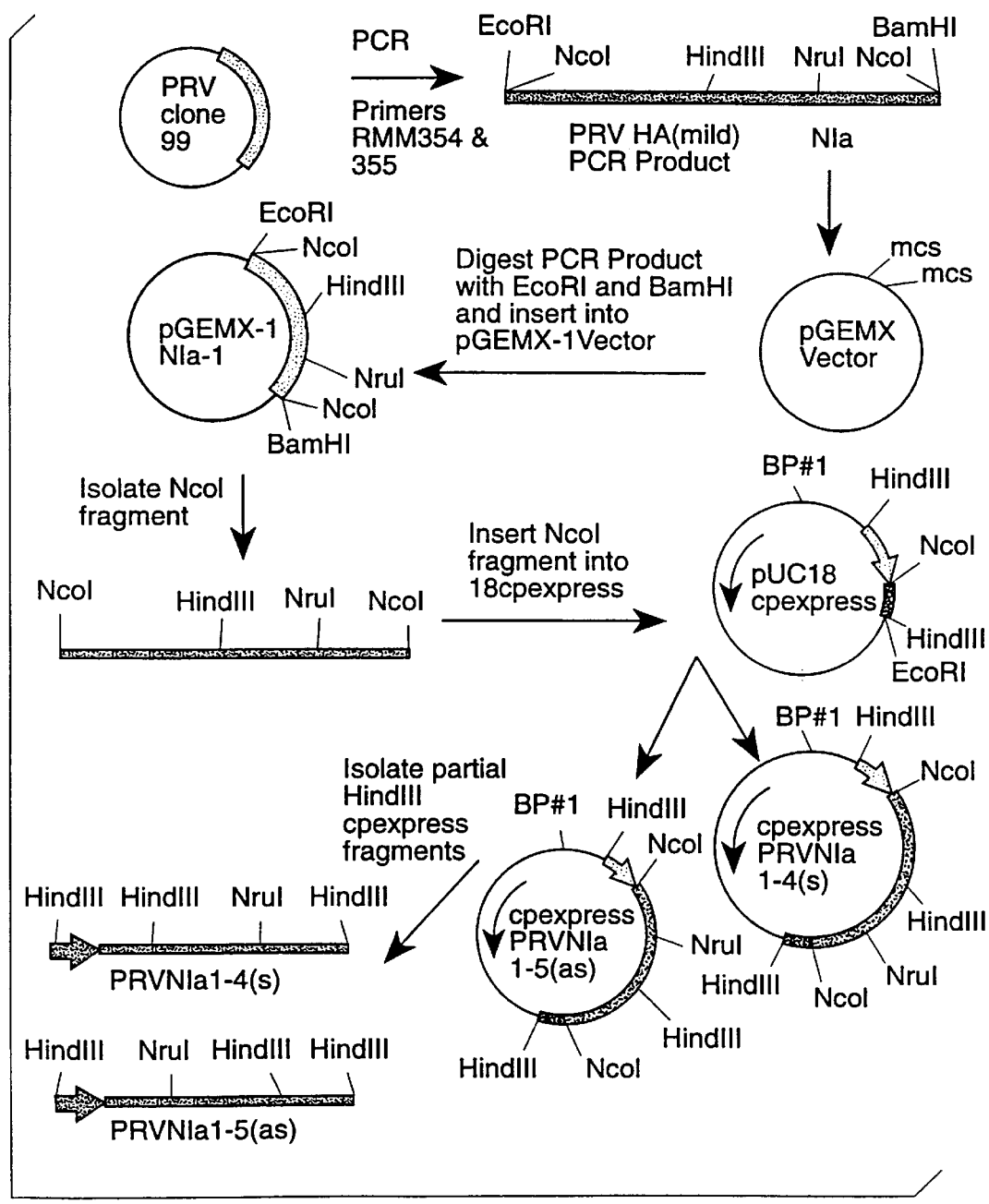
FIGS. 7A and 7B. A schematic representation of the cloning strategy for PRV USA P-type (HA attenuated) gene expression cassettes.
Figure 7B:
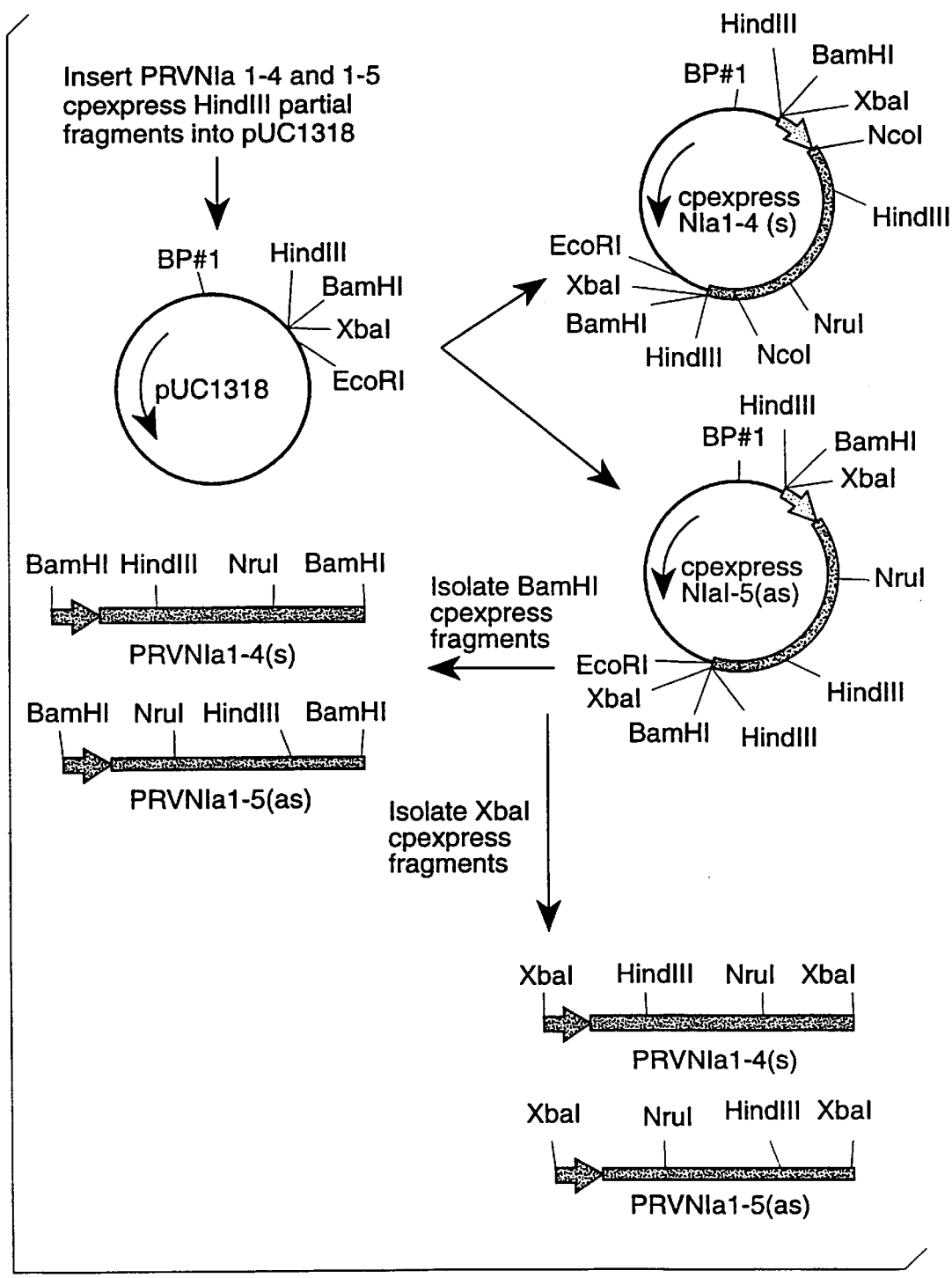

A cDNA clone (#99) obtained from D. Gonsalves at Cornell University of the 3' end of PRV USA P-type (HA attenuated) strain served as a PCR template to amplify a PRV region that included 189 bp of the 3' end of the CI gene, the entire VpG gene, the entire NIa protease gene, and 146 bp of the 5' end of NIb gene (FIGS. 5A–5C). Primers RMM354 and RMM355 [SEQ ID NO: 3 and 4, respectively] were used during the PCR amplification to introduce novel restriction sites at each end of the PRV segment engineered. The resulting PCR-amplified segment was digested with EcoRI and BamHI (see FIGS. 2A–2C and 5A–5C) and cloned by inserting it into the vector pGEMX-1 (Promega, Madison, Wis.). The PRV sequences in a resulting clone (pGEMX-1 NIa-1) were nucleotide-sequenced (FIGS. 5A–5C; [SEQ ID NO: 5]). There were no sequence differences between the sequence of clone 99 and clone pGEMX-1 NIa-1.

pGEMX-1 NIa-1 was digested with NcoI and the resulting NcoI fragment isolated for insertion into the expression cassette pUC18cpexpress. Both sense and antisense clones of expression cassettes (the expression cassettes are designated cpexpress PRV NIa 1-4 for the sense orientation and cpexpress PRV NIa 1-5 for the antisense orientation) containing the NcoI fragment of PRV were isolated. The plasmid containing the antisense orientation cassette is known as pUC18cpexpressPRVNIa1-5. The plasmid containing the sense orientation cassette is known as pUC18cpexpressPRVNIa1-4. Subsequently, the HindIII fragments containing expression cassettes from each pUC18 plasmid containing either expression cassette were inserted into the HindIII site of pUC1318 (clone pUC1318cpexpressPRVNIa1-4 and pUC1318cpexpressPRVNIa1-5) to provide additional sites for installing cassettes into binary plasmids (FIGS. 7A–7B). Subsequently, both XbaI and BamHI fragments were isolated from pUC1318cpexpressPRVNIa1-4 and pUC1318cpexpressPRVNIa1-5. These fragments were inserted into the corresponding XbaI or BglII sites of pGA482G, pEPG111, pEPG106, pEPG109, pEPG120, or pEGG252 (Table 1).

Resulting binary plasmids were transformed into *Agrobacteria tumefaciens* strains Mog301 and C58Z707.

Figure 8A:
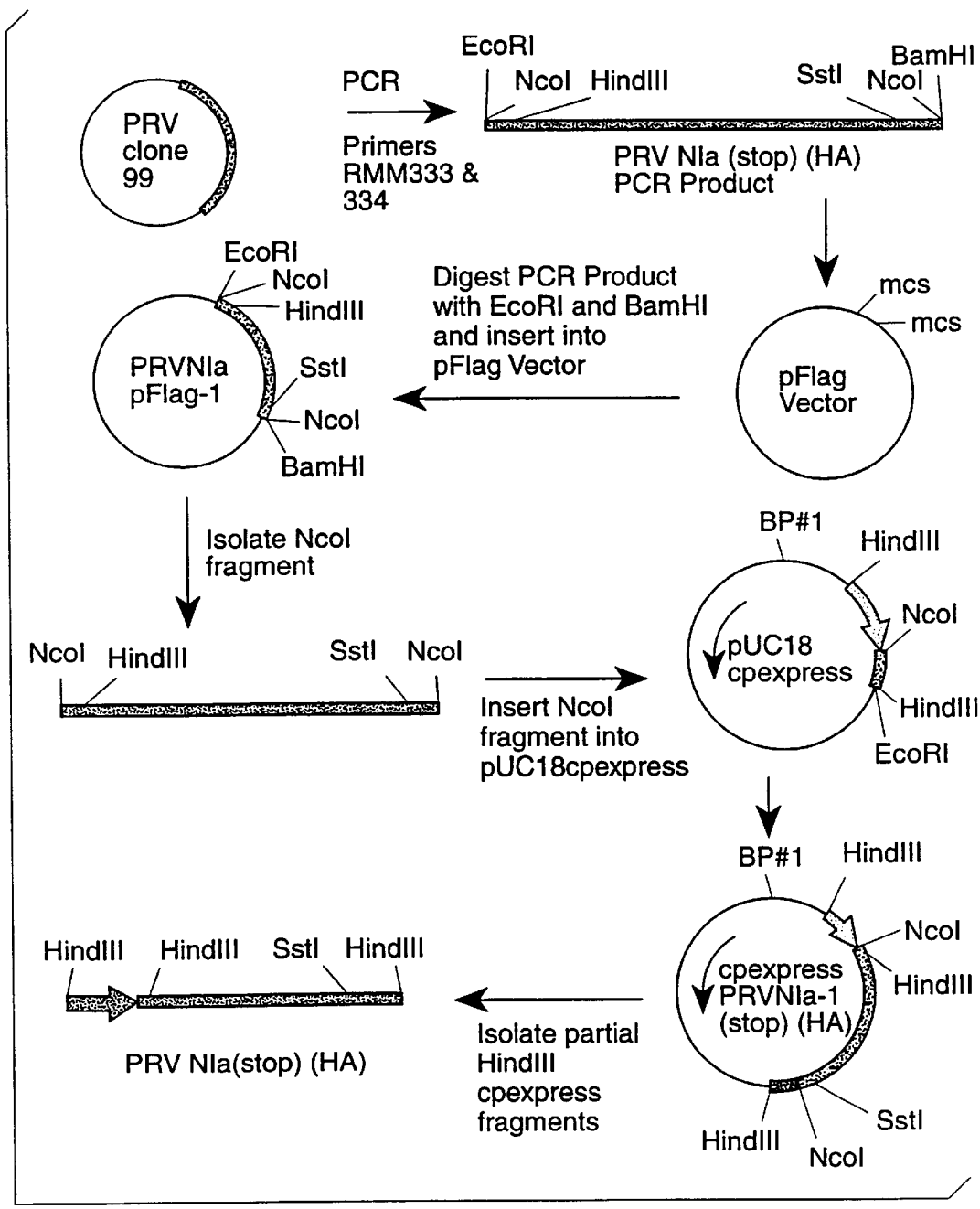
Figure 8B:
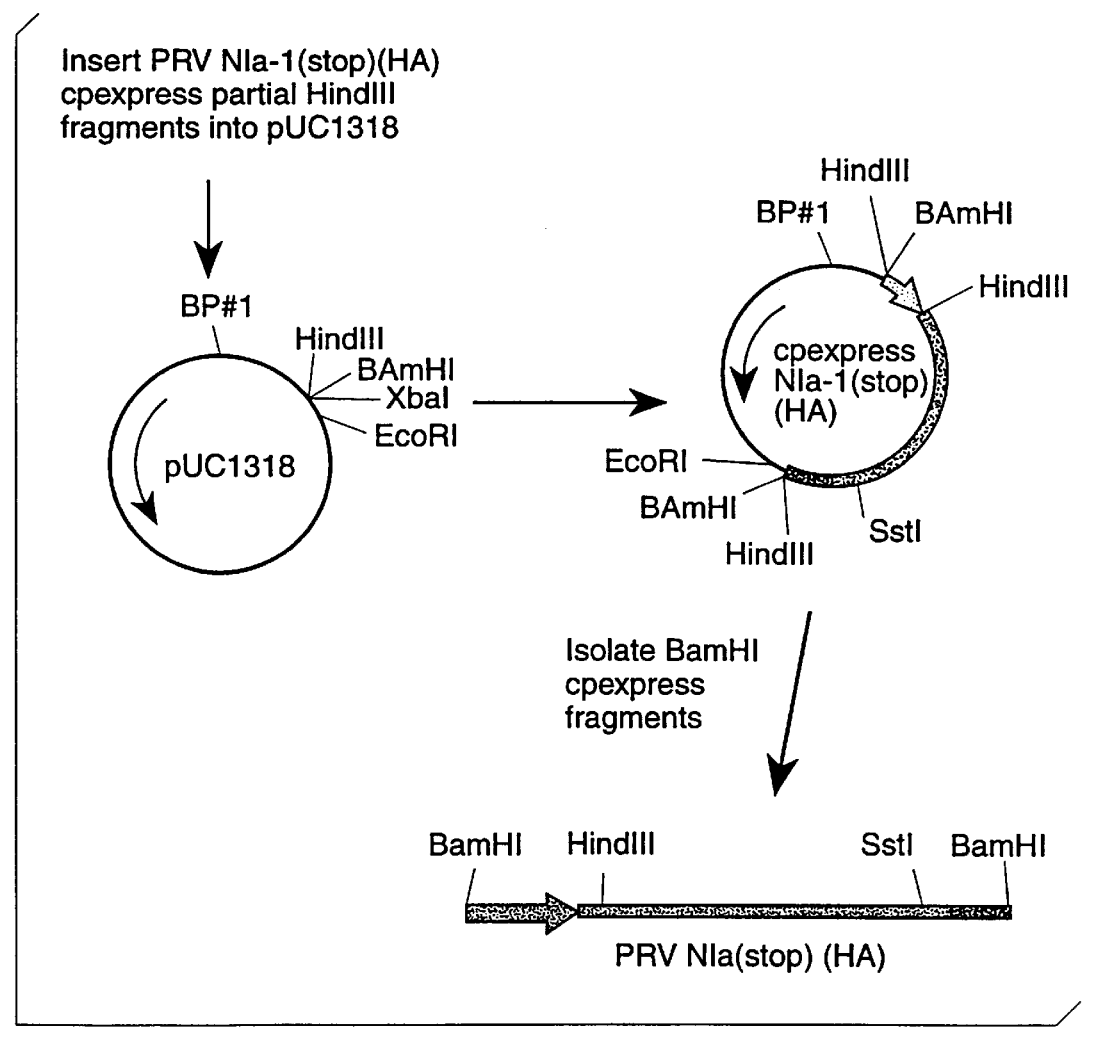

A PRV USA P-type (HA attenuated) NIa gene cassette was prepared that included an introduced stop codon (FIGS. 8A–8B). To prepare the NIa coding sequence for insertion into the expression cassette pUC18cpexpress, novel restriction sites were introduced with oligomer primers RMM333 and RMM334 (see FIGS. 4A–4B [SEQ ID NO: 10 and 11, respectively]). In addition, RMM333 introduced a single base pair deletion which results in a stop codon near the translation start site. The fragment amplified by oligomer pair RMM333 and RMM334 is 1339 base pairs in length and is shown in FIGS. 8A–8B. After PCR amplification, the fragment was engineered to obtain the cassette PRVNIa-1 (stop) (HA) as shown in FIG. 8. The cassette was inserted into binary plasmids as described in Table 1.

TABLE 1

| Binary | Parental Plasmid | Site | PRV NIa Cassette | pEPG# |
|---|---|---|---|---|
| pGA482G | pEPG120 (CMVwl62G) | XbaI | PRVNIa1-4 (s) | (HA)200 |
| pGA482G | pEPG120 (CMVwl62G) | XbaI | PRVNIa1-5 (asdouble) | (HA)201 |
| pGA482G | pGA482G | XbaI | PRVNIa1-5 (as) | (HA)202 |
| pPRBN | pEPG109 (CWL41/Z/W) | XbaI | PRVNIa1-4 (s) | (HA)113 |
| pPRBN | pEPG109 (CWL41/Z/W) | XbaI | PRVNIa1-5 (as) | (HA)114 |
| pPRBN | pEPG111 (C/Z/W) | BglII | PRVNIa1-4 (s) | (HA)224 |
| pPRBN | pEPG111 (C/Z/W) | BglII | PRVNIa1-5 (as) | (HA)225 |
| pPRBN | pEPG106 (ZW) | BglII | PRVNIa1-4 (s) | (HA)226 |
| pPRBN | pEPG106 (ZW) | BglII | PRVNIa1-5 (as) | (HA)227 |

C. Transfer of PRV Protease Genes to Plants

Agrobacterium-mediated transfer of the plant expressible PRV protease genes described herein was done using the methods described in PCT published application WO 89/05859, entitled "Agrobacterium Mediated Transformation of Germinating Plant Seeds."

Transgenic cucumber lines have been produced with the USA P-type (HA-attenuated) PRV NIa gene construct described above. Progeny of $R_0$ transgenic plants were challenged in the greenhouse. Challenge results indicate that PRV USA P-type NIa transgenic $R_1$ plants are protected to a significant extent against both homologous PRV challenge and heterologous PRV challenge. Compared with non-transgenic controls, transgenic $R_1$ progeny show delayed onset and reduced symptoms on cucumber leaves and fruits.

The transgenic status of these plants was verified by their growth and development on media containing kanamycin and polymerase chain reaction amplification of the integrated transgenes. All squash and cucumber transgenic lines tested were positive for the NPTII gene by PCR. Most cantaloupe lines (>90%) were positive for NPTII by PCR. Most (>85%) plants positive for NPTII by PCR also tested positive for NIa sequences.

Some cucumber plants transgenic for the constructs in pEPG200 PRV NIa showed delayed onset and reduced PRV symptom severity (Tables I, II, and V), while other cucumber lines transgenic for pEPG200 showed no delay in the onset of symptoms or reduction of severity (Tables III and IV). Cucumber lines transgenic for PRV coat protein genes showed a reduction of symptom severity (for examples see Tables VI–VIII). However, if both NIa and CP genes are introduced into the same plant by sexual hybridization, resulting progeny are highly resistant to PRV infection. Consider progeny from the cross: MS642-93321-212-56-7

X MS642-93190-200-1-13. The construct pEPG212 includes PRVwmcp16(s)/Cw141/ ZYE72/WMBn22, and the construct pEPG200 includes PRVhNIaI-4(s)/CMVwl62-G. Progeny that include both constructs are essentially resistant to PRV. Progeny show resistance to PRV isolated from Florida (FLA83) and California.

Accordingly, both coat protein and protease genes incorporated into the same plant by sexual hybridization provide high levels of protection to PRV. Numerous binary plasmids were prepared that included both PRV coat protein and protease genes for transformation into plants. By this procedure both genes were incorporated into the same plant without the need for sexual hybridization. Instead, both genes were introduced by a single gene transfer (transformation) experiment.

PCR Results: Ro plants were tested for PRV NIa transgene integration by PCR amplifying genes positioned at either end of the inserted blocks of construct.

Left Border|NPTII| |PRV NIa|CMV CP|Right Border

For transgenic plants (squash, cucumber, and melon) the presence of PRV NIa was established by PCR detection of NPTII and CMV CP (see map, above). These results indicate that if both NPTII and CMV CP genes are detected, genes internal to these two are also present.

Summary of PCR results of plants transformed with constructs containing PRV NIa constructions

| Construct | NPTII+/CMV+ | NPTII+/CMW- |
|---|---|---|
| pEPG232 | 14 | 4 |
| pEPG200 | 31 | 1 |
| pEPG114 | 14 | 4 |
| pEPG113 | 33 | 6 |
| pEPG224 | 9 | 0 |
| pEPG250 | 4 | 0 |

In some cases PRV NIa was tested for directly, however, in all cases both NPTII and CMV CP were assayed by PCR. This table shows squash, melon, and cantaloupe plants transformed with binary plasmid listed in the first column. These PRV NIa constructs. The second column indicates numbers of plants in which both NPTII and CMV coast protein genes were identified by PCR. The third column indicates numbers of plants which were positive for the NPTII gene and negative for CMV coat protein. Eighty six percent of plants testing NPTII+ were positive for the CMV CP gene.

Details on the cucumber cross MS642-93321-212-56-7 X MS 642-93190-200-1-13. Below we give protection data for progeny of this cross. The challenge virus indicates which isolate of PRV was used to challenge transgenic progeny of the indicated cross. Plant No. indicates the progeny number of the cross. Each of the three challenges listed below is a separate experiment. Each challenge experiment included separate individual progeny from the above cross. For example, plant number "1" in the PRV-FLA83 challenge is a different plant than plant number "1": in the PRV-CA challenge. PCR results are summarized in the CP/NIa column. Both PRV coat protein and PRV NIa were assayed by PCR. A "+" indicates that the gene was identified, and a "−" indicates that by PCR no gene was identified. Disease rating was carried out 17, 14 and 31 days post inoculation (DPI). Disease ratings range from 0 (no symptoms) to 7 (severe symptoms). NT indicates that the progeny challenged were not tested by PCR.

TABLE I

| Challenge Virus | Plant No. | CP/NIa | DPI Disease Rating 17 | 24 | 31 |
|---|---|---|---|---|---|
| PRV-FLA83 | 1 | +/+ | 0 | 0 | 0 |
|  | 2 | −/− | 5 | 5 | 5 |
|  | 3 | −/− | 5 | 5 | 5 |
|  | 4 | +/+ | 0 | 0 | 0 |
|  | 5 | +/− | 0 | 3 | 3 |
|  | 6 | NT | 5 | 5 | 5 |
|  | 7 | NT | 5 | 5 | 5 |
|  | 8 | NT | 5 | 5 | 5 |
|  | 9 | NT | 5 | 3 | 3 |
|  | 10 | NT | 3 | 3 | 5 |
|  | 11 | NT | 0 | 0 | 0 |
|  | 12 | NT | 3 | 3 | 3 |
|  | 13 | NT | 5 | 3 | 3 |
|  | 14 | NT | 0 | 0 | 0 |
| PRV-CA | 1 | −/− | 3 | 5 | 5 |
|  | 2 | +/− | 3 | 5 | 5 |
|  | 3 | +/+ | 0 | 0 | 0 |
|  | 4 | +/− | 3 | 3 | 3 |
|  | 5 | −/+ | 3 | 3 | 5 |
|  | 6 | −/− | 3 | 3 | 3 |
|  | 7 | +/+ | 0 | 0 | 0 |
|  | 8 | +/− | 3 | 5 | 3 |
|  | 9 | +/− | 3 | 5 | 5 |
|  | 10 | +/+ | 0 | 0 | 0 |
|  | 11 | NT | 3 | 3 | 3 |
|  | 12 | NT | 1 | 5 | 3 |
|  | 13 | NT | 3 | 5 | 5 |
| PRV-NC | 1 | NT | 3 | 5 | 5 |
|  | 2 | NT | 3 | 5 | 5 |
|  | 3 | NT | 0 | 5 | 5 |
|  | 4 | NT | 3 | 5 | 5 |
|  | 5 | NT | 3 | 5 | 3 |
|  | 6 | NT | 3 | 3 | 3 |
|  | 7 | NT | 0 | 3 | 3 |
|  | 8 | NT | 0 | 3 | 3 |
|  | 9 | NT | 0 | 3 | 3 |
|  | 10 | NT | 3 | 5 | 7 |
|  | 11 | NT | 0 | 3 | 3 |
|  | 12 | NT | 3 | 5 | 5 |
|  | 13 | NT | 3 | 5 | 5 |

PRVH-NIa 1–4(s)/CMVWL-62-G

| Line | Virus | DPI | NPT-II | Ratio | Symptomatic Plants (%) | Disease Rating |
|---|---|---|---|---|---|---|
| MS642-93130-200-8 | PRV-FL | 12 | + | 0/6 | (0) | 0.0 |
|  |  |  | − | 6/7 | (87) | 3.1 |
|  | PRV-TX |  | + | 0/6 | (0) | 0.0 |
|  |  |  | − | 4/5 | (80) | 2.4 |
|  | PRV-NC |  | + | 6/12 | (50) | 0.5 |
|  |  |  | − | 3/3 | (100) | 1.0 |
|  | PRV-FL | 16 | + | 0/6 | (0) | 0.0 |
|  |  |  | − | 6/7 | (87) | 4.3 |
|  | PRV-TX |  | + | 1/6 | (17) | 0.2 |
|  |  |  | − | 4/5 | (80) | 2.4 |
|  | PRV-NC |  | + | 12/12 | (100) | 5.9 |
|  |  |  | − | 3/3 | (100) | 7.0 |
|  | PRV-FL | 19 | + | 0/6 | (0) | 0.0 |
|  |  |  | − | 6/7 | (87) | 4.0 |
|  | PRV-TX |  | + | 1/6 | (17) | 0.2 |
|  |  |  | − | 4/5 | (80) | 2.4 |
|  | PRV-NC |  | + | 12/12 | (100) | 1.0 |
|  |  |  | − | 3/3 | (100) | 7.0 |

TABLE II

PRVH-NIa 1–4(s)/CMVWL62-G

| Line | Virus | DPI | NPT-II | Symptomatic Plants Ratio | (%) | Disease Rating |
|---|---|---|---|---|---|---|
| GA715-93190-200-70 | PRV-FL | 10 | + | 0/9 | (0) | 0.0 |
| | | | − | 6/6 | (100) | 5.0 |
| | PRV-CA | | + | 1/9 | (9) | 0.6 |
| | | | − | 5/6 | (83) | 4.5 |
| | PRV-FL | 16 | + | 3/9 | (33) | 1.0 |
| | | | − | 5/5 | (100) | 5.0 |
| | PRV-CA | | + | 8/9 | (89) | 3.3 |
| | | | − | 6/6 | (100) | 4.7 |
| | PRV-FL | 23 | + | 8/9 | (89) | 4.4 |
| | | | − | 5/5 | (100) | 5.0 |
| | PRV-CA | | + | 9/9 | (100) | 3.4 |
| | | | − | 6/6 | (100) | 5.0 |

TABLE III

PRVH-NIa 1–4(s)/CMVWL62-G

| Line | Virus | DPI | NPT-II | Symptomatic Plants Ratio | (%) | Disease Rating |
|---|---|---|---|---|---|---|
| MSCY2-93190-200-1 | PRV-CA | 8 | + | 0/10 | (0) | 0.0 |
| | | | − | 3/3 | (100) | 5.0 |
| | PRV-CA | 12 | + | 10/10 | (100) | 3.0 |
| | | | − | 3/3 | (100) | 5.0 |
| | PRV-CA | 17 | + | 10/10 | (100) | 3.0 |
| | | | − | 3/3 | (100) | 5.0 |

TABLE IV

PRVh NIa 1–4(S)/CMVML62-G

| Line | Virus | DPI | NPT-II | Symptomatic Plants Ratio | (%) | Disease Rating |
|---|---|---|---|---|---|---|
| GA715-93190-200-68 | PRV-FL | 12 | + | 0/5 | (0) | 0.0 |
| | | | − | 9/9 | (100) | 3.0 |
| | PRV-CA | | + | 0/6 | (0) | 0.0 |
| | | | − | 7/7 | (100) | 6.7 |
| | PRV-TX | | + | 0/4 | (0) | 0.0 |
| | | | − | 8/9 | (88) | 2.7 |
| | PRV-FL | 19 | + | 0/5 | (0) | 0.0 |
| | | | − | 9/9 | (100) | 5.8 |
| | PRV-CA | | + | 0/6 | (0) | 0.0 |
| | | | − | 7/7 | (100) | 7.0 |
| | PRV-TX | | + | 0/4 | (0) | 0.0 |
| | | | − | 8/9 | (88) | 4.1 |
| | PRV-FL | 28 | + | 0/5 | (0) | 0.0 |
| | | | − | 9/9 | (100) | 5.7 |
| | PRV-CA | | + | 0/6 | (0) | 0.0 |
| | | | − | 7/7 | (100) | 7.0 |
| | PRV-TX | | + | 0/4 | (0) | 0.0 |
| | | | − | 8/9 | (88) | 3.9 |

TABLE V

PNIa22/CWL41/ZY72/WMBW22

| Line | Virus | DPI | NPT-II | Symptomatic Plants Ratio | (%) | Disease Rating |
|---|---|---|---|---|---|---|
| GA14A-93281-113-6 | PRV-FL | 12 | + | 0/9 | (0) | 0.0 |
| | | | − | 4/4 | (100) | 3.0 |
| | PRV-CA | | + | 0/7 | (0) | 0.0 |
| | | | − | 6/6 | (100) | 6.3 |
| | PRV-TX | | + | 0/8 | (0) | 0.0 |
| | | | − | 4/6 | (67) | 2.0 |

TABLE V-continued

PNIa22/CWL41/ZY72/WMBW22

| Line | Virus | DPI | NPT-II | Symptomatic Plants Ratio | (%) | Disease Rating |
|---|---|---|---|---|---|---|
| | PRV-NC | | + | 0/7 | (0) | 0.0 |
| | | | − | 4/8 | (50) | 2.4 |
| | PRV-FL | 19 | + | 7/9 | (77) | 2.7 |
| | | | − | 4/4 | (100) | 4.5 |
| | PRV-CA | | + | 5/7 | (71) | 2.7 |
| | | | − | 6/6 | (100) | 5.0 |
| | PRV-TX | | + | 2/8 | (16) | 0.5 |
| | | | − | 4/5 | (80) | 3.6 |
| | PRV-NC | | + | 3/7 | (43) | 1.1 |
| | | | − | 5/5 | (100) | 5.0 |
| | PRV-FL | 21 | + | 7/9 | (77) | 3.2 |
| | | | − | 4/4 | (100) | 5.0 |
| | PRV-CA | | + | 5/7 | (71) | 3.3 |
| | | | − | 6/6 | (100) | 5.0 |
| | PRV-TX | | + | 4/8 | (50) | 1.8 |
| | | | − | 6/6 | (100) | 4.3 |
| | PRV-NC | | + | 6/7 | (86) | 4.3 |
| | | | − | 5/5 | (100) | 7.0 |

TABLE VI

PRVWMCP16(S)/CWL/ZY72/WMBN22

| Line | Virus | DPI | NPT-II | Symptomatic Plants Ratio | (%) | Disease Rating |
|---|---|---|---|---|---|---|
| MS642-93316-212-12 | PRV-FL | 4 | + | 0/8 | (0) | 0.0 |
| | | | − | 6/7 | (86) | 4.3 |
| | PRV-CA | | + | 0/4 | (0) | 0.0 |
| | | | − | 11/11 | (100) | 4.5 |
| | PRV-TX | | + | 0/9 | (0) | 0.0 |
| | | | − | 0/6 | (0) | 0.0 |
| | PRV-NC | | + | 0/9 | (0) | 0.0 |
| | | | − | 0/3 | (0) | 0.0 |
| | PRV-FL | 12 | + | 8/8 | (100) | 3.5 |
| | | | − | 7/7 | (100) | 4.4 |
| | PRV-CA | | + | 4/4 | (100) | 5.0 |
| | | | − | 11/11 | (100) | 5.0 |
| | PRV-TX | | + | 8/9 | (89) | 2.7 |
| | | | − | 6/6 | (100) | 3.0 |
| | PRV-NC | | + | 0/9 | (0) | 0.0 |
| | | | − | 0/6 | (0) | 0.0 |
| | PRV-FL | 20 | + | 8/8 | (100) | 3.7 |
| | | | − | 7/7 | (100) | 4.3 |
| | PRV-CA | | + | 4/4 | (100) | 3.5 |
| | | | − | 11/11 | (100) | 5.0 |
| | PRV-TX | | + | 9/9 | (100) | 4.8 |
| | | | − | 6/6 | (100) | 4.3 |
| | PRV-NC | | + | 9/9 | (100) | 4.8 |
| | | | − | 3/3 | (100) | 3.7 |

TABLE VII

PRVWMCP16(S)/CWL/ZY72/WMBN22

| Line | Virus | DPI | NPT-II | Symptomatic Plants Ratio | (%) | Disease Rating |
|---|---|---|---|---|---|---|
| MSGY2-93321-212-56 | PRV-FL | 14 | + | 6/6 | (100) | 3.3 |
| | | | − | 8/8 | (100) | 5.0 |
| | PRV-CA | | + | 8/8 | (100) | 5.3 |
| | | | − | 5/5 | (100) | 5.4 |
| | PRV-FL | 17 | + | 6/6 | (100) | 3.0 |
| | | | − | 8/8 | (100) | 5.0 |

TABLE VII-continued

PRVWMCP16(S)/CWL/ZY72/WMBN22

| Line | Virus | DPI | NPT-II | Symptomatic Plants Ratio | (%) | Disease Rating |
|------|-------|-----|--------|--------------------------|-----|----------------|
|      | PRV-CA |     | +      | 7/7                      | (100) | 3.0 |
|      |        |     | −      | 5/5                      | (100) | 5.0 |
|      | PRV-FL | 21  | +      | 6/6                      | (100) | 3.0 |
|      |        |     | −      | 8/8                      | (100) | 5.0 |
|      | PRV-CA |     | +      | 7/7                      | (100) | 3.9 |
|      |        |     | −      | 5/5                      | (100) | 5.4 |

TABLE VIII

PRVwmcp16 (S)/CWL/ZY72/WMBN22

| Line | Virus | DPI | NPT-II | Symptomatic Plants Ratio | (%) | Disease Rating |
|------|-------|-----|--------|--------------------------|-----|----------------|
| GA715-93293-212-21 | PRV-FL | 13 | + | 1/3 | (33) | 1.0 |
|      |        |     | −      | 7/7 | (100) | 4.7 |
|      | PRV-CA |     | +      | 2/4 | (50)  | 0.5 |
|      |        |     | −      | 5/6 | (83)  | 4.2 |
|      | PRV-TX |     | +      | 0/2 | (0)   | 0.0 |
|      |        |     | −      | 0/8 | (0)   | 0.0 |
|      | PRV-NC |     | +      | 0/3 | (0)   | 0.0 |
|      |        |     | −      | 0/7 | (0)   | 0.0 |
|      | PRV-FL | 16  | +      | 3/3 | (100) | 3.0 |
|      |        |     | −      | 7/7 | (100) | 5.0 |
|      | PRV-CA |     | +      | 4/4 | (100) | 4.5 |
|      |        |     | −      | 6/6 | (100) | 6.7 |
|      | PRV-TX |     | +      | 2/2 | (100) | 1.0 |
|      |        |     | −      | 8/8 | (100) | 1.0 |
|      | PRV-NC |     | +      | 3/3 | (100) | 3.0 |
|      |        |     | −      | 7/7 | (100) | 3.0 |
|      | PRV-FL | 29  | +      | 3/3 | (100) | 5.0 |
|      |        |     | −      | 7/7 | (100) | 5.9 |
|      | PRV-CA |     | +      | 4/4 | (100) | 5.0 |
|      |        |     | −      | 6/6 | (100) | 7.0 |
|      | PRV-TX |     | +      | 2/2 | (100) | 3.0 |
|      |        |     | −      | 8/8 | (100) | 3.0 |
|      | PRV-CA |     | +      | 3/3 | (100) | 5.0 |
|      |        |     | −      | 7/7 | (100) | 5.9 |

TABLE 9A

| INBRED | CONSTRUCT | PRV-W-FL83 | PRV-W-CA |
|--------|-----------|------------|----------|
| CA40   | −         | 3/3        |          |
|        | +         | 12/12      |          |
|        | −         |            |          |
|        | +         | 14/15      |          |
|        | −         | 7/7        |          |
|        | −         | 4/4        |          |
|        | −         | 2/2        |          |
|        | +         | 10/13      |          |
| GA715  | −         |            | 3/3      |
|        | +         |            | 4/4      |
|        | −         |            | 7/7      |
|        | +         |            | 8/8      |
|        | −         | 2/2        |          |
|        | +         | 6/6        |          |
|        | −         |            | 7/7      |
|        | +         |            | 0/8      |
|        | −         |            | 7/7      |
|        | +         | 11/11      | 8/8      |
| GP14A  | +         | 3/3        |          |
|        | −         |            |          |
|        | +         | 10/10      |          |
|        | −         | 3/3        |          |
|        | −         | 5/5        |          |
|        | +         | 9/9        |          |

TABLE 9A-continued

| INBRED | CONSTRUCT | PRV-W-FL83 | PRV-W-CA |
|--------|-----------|------------|----------|
|        | −         | 5/5        |          |
|        | +         | 7/8        |          |
| MS642  | −         | 1/1        | 3/3      |
|        | +         | 3/3        | 10/10    |
|        | −         | 11/11      | 4/4      |
|        | +         | 2/2        | 6/8      |
|        | −         |            | 9/9      |
|        | +         | 5/5        | 1/5      |
|        | −         | 13/13      | 8/8      |
|        | +         | 2/2        | 7/7      |
|        | −         | 6/6        | 5/5      |
|        | +         | 6/6        | 6/6      |
|        | +         |            |          |
|        | −         |            |          |
|        | −         | 8/8        | 5/5      |
|        | +         | 6/6        | 7/7      |
|        | +         | 10/10      | 5/5      |
|        | −         | 5/5        | 10/10    |
|        | −         | 5/5        | 5/5      |
|        | +         | 7/7        | 7/7      |
|        | −         |            |          |
|        | +         |            |          |
|        | −         | 2/2        |          |
|        | +         | 12/12      |          |
| V1151  | +         |            |          |
|        | −         |            |          |
| V3893  | +         | 8/8        |          |
|        | −         | 6/6        |          |
| V4306  | +         | 8/8        |          |
|        | −         | 3/3        |          |
|        | −         | 10/10      |          |
|        | +         | 5/5        |          |
|        | +         |            |          |
|        | −         |            |          |
|        | −         | 1/1        |          |
|        | +         | 12/13      |          |
|        | +         |            |          |
|        | −         |            |          |
|        | +         | 4/4        |          |
|        | −         | 7/7        |          |
|        | +         |            |          |
|        | −         |            |          |
|        | +         | 7/7        |          |
|        | −         | 7/7        |          |
|        | −         | 6/8        |          |
|        | +         | 2/2        |          |
|        | +         | 11/11      |          |
|        | −         | 4/4        |          |
| YC77E  | −         |            |          |
|        | +         |            |          |
| CA95   | −         | 0/2        |          |
|        | −         |            |          |
|        | +         |            |          |
|        | +         | 0/12       |          |
|        | −         | 0/3        |          |
|        | +         |            |          |
|        | −         |            |          |
| GA715  | +         |            |          |
|        | −         |            |          |
|        | −         |            |          |
|        | +         |            |          |
|        | −         | 5/5        | 8/8      |
|        | +         | 7/7        | 4/5      |
|        | +         | 4/4        | 4/4      |
|        | −         | 8/8        | 10/10    |
|        | −         | 5/5        | 6/6      |
|        | +         | 5/5        | 4/4      |
|        | −         | 7/7        | 4/4      |
|        | +         | 3/3        | 6/6      |
| GP14A  | +         | 5/5        |          |
|        | −         | 7/7        |          |
|        | −         |            |          |
|        | +         |            |          |
|        | +         | 5/5        | 5/5      |
|        | −         | 8/8        | 7/7      |

TABLE 9A-continued

| INBRED | CONSTRUCT | PRV-W-FL83 | PRV-W-CA |
|---|---|---|---|
|  | + | 7/8 | 4/4 |
|  | − | 2/2 | 5/5 |
|  | − | 1/1 | 3/3 |
|  | + | 11/11 | 9/9 |
|  | + |  |  |
|  | − |  |  |
| MP56 | + | 1/6 |  |
|  | − | 3/3 |  |
|  | + | 3/3 |  |
|  | − | 7/7 |  |
|  | + |  |  |
|  | − |  |  |
|  | + |  |  |
|  | − |  |  |
|  | + | 1/8 |  |
|  | − | 6/6 |  |
|  | − | 5/15 |  |
|  | + |  |  |
|  | − | 6/6 |  |
|  | + | 9/9 |  |
| CA10 | − |  |  |
|  | + | 8/11 |  |
|  | − | 2/2 |  |
|  | + | 8/8 |  |
|  | − |  |  |
|  | − |  |  |
|  | + |  |  |
|  | − |  |  |
|  | + |  |  |
| CA100 | − |  |  |
|  | + |  |  |
|  | + |  |  |
|  | − |  |  |
| CA111 | + |  |  |
| CA14 | + | 10/10 |  |
|  | − | 4/4 |  |
|  | − |  |  |
|  | + |  |  |
| CA24 | + | 15/15 |  |
|  | − |  |  |
| CA40 | + | 6/6 |  |
|  | − | 4/4 |  |
|  | + |  |  |
|  | − |  |  |
|  | + |  |  |
|  | − |  |  |
|  | + |  |  |
|  | − |  |  |
|  | + | 8/8 |  |
|  | − | 5/5 |  |
| CA40/100 | + |  |  |
|  | − |  |  |
| CA76 | − |  |  |
|  | + |  |  |
|  | + |  |  |
|  | − |  |  |
|  | − |  |  |
|  | + |  |  |
| CA95 | − |  |  |
|  | + |  |  |
|  | − | 0/4 |  |
|  | + | 0/11 |  |
|  | + | 0/12 |  |

All publications, patents and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A vector comprising a chimeric expression cassette comprising an isolated and purified DNA molecule comprising DNA encoding the NIa protease of the FLA 83 W-type strain of papaya ringspot virus and at least one chimeric expression cassette comprising an isolated and purified DNA molecule comprising DNA encoding a coat protein, wherein each expression cassette comprises a promoter and a polyadenylation signal wherein the promoter is operably linked to the DNA molecule and the DNA molecule is operably linked to the polyadenylation signal.

2. The vector of claim 1 wherein the FLA83 W-type strain of papaya ringspot virus has the nucleotide sequence shown in SEQ ID NO: 1.

3. The vector of claim 1 wherein the promoter is the cauliflower mosaic virus 35S promoter.

4. The vector of claim 3 wherein the polyadenylation signal is the polyadenylation signal of the cauliflower mosaic 35S gene.

5. The vector of claim 1 wherein the DNA encoding the coat protein is from papaya ringspot virus, cucumber mosaic virus, zucchini yellow mosaic virus or watermelon mosaic virus 2.

6. A bacterial cell comprising the vector of claim 1.

7. The bacterial cell of claim 6 wherein the bacterial cell is selected from the group consisting of an *Agrobacterium tumefaciens* cell and an *Agrobacterium rhizogenes* cell.

8. A transformed plant cell transformed with the vector of claim 1.

9. The transformed plant cell of claim 8 wherein the promoter is cauliflower mosaic virus 35S promoter is cauliflower mosaic virus 35S promoter and the polyadenylation signal is the polyadenylation signal of the cauliflower mosaic 35S gene.

10. A plant selected from the family Cucurbitaceae comprising at least one transformed cell of claim 8.

11. A vector comprising a chimeric expression cassette comprising an isolated and purified DNA molecule comprising DNA encoding the NIa protease of the USA P-type (HA attenuated) strain of papaya ringspot virus and at least one chimeric expression cassette comprising an isolated and purified DNA molecule comprising DNA encoding a coat protein, wherein each expression cassette comprises a promoter and a polyadenylation signal wherein the promoter is operably linked to the DNA molecule and the DNA molecule is operably linked to the polyadenylation signal.

12. The vector of claim 11 wherein the USA P-type (HA attenuated) strain of papaya ringspot virus has the nucleotide sequence shown in SEQ ID NO: 5.

13. The vector of claim 11 wherein the promoter is the cauliflower mosaic virus 35S promoter.

14. The vector of claim 13 wherein the polyadenylation signal is the polyadenylation signal of the cauliflower mosaic 35S gene.

15. The vector of claim 11 wherein the DNA encoding the coat protein is from papaya ringspot virus, cucumber mosaic virus, virus zucchini yellow mosaic virus or watermelon mosaic virus 2.

16. A bacterial cell comprising the vector of claim 11.

17. The bacterial cell of claim 16 wherein the bacterial cell is selected from the group consisting of an *Agrobacterium tumefaciens* cell and an *Agrobacterium rhizogenes* cell.

18. A transformed plant cell transformed with the vector of claim 11.

19. The transformed plant cell of claim 18 wherein the promoter is cauliflower mosaic virus 35S promoter is cauliflower mosaic virus 35S promoter and the polyadenylation signal is the polyadenylation signal of the cauliflower mosaic 35S gene.

20. A plant selected from the family Cucurbitaceae comprising at least one transformed cell of claim 18.

21. A method of preparing a papaya ringspot viral resistant plant comprising:

(a) transforming plant cells with a chimeric expression cassette comprising a promoter functional in plant cells operably linked to a DNA molecule that encodes a protease wherein the DNA molecule comprises DNA encoding the NIa protease selected from the group consisting of FLA 83 W-type strain and USA P-type (HA attenuated) strain of papaya ringspot virus and at least one chimeric expression cassette comprising a promoter functional in plant cells operably linked to a DNA molecule that encodes a coat protein;

(b) regenerating the plant cells to provide a differentiated plant; and (c) identifying a transformed plant that expresses the papaya ringspot protease gene at a level sufficient to render the plant resistant to infection to papaya ringspot virus.

22. The method of claim 20 wherein the FLA 83 W-type strain of papaya ringspot has the nucleotide sequence shown in SEQ ID NO: 1 and the USA P-type (HA attenuated) strain of papaya ringspot has the nucleotide sequence shown in SEQ ID NO:5.

23. The method of claim 20 wherein the plant is a dicot.

24. The method of claim 20 wherein the dicot is selected from the family Cucurbitaceae.

25. The method of claim 21 wherein the DNA molecule encoding the coat protein is from papaya ringspot virus, cucumber mosaic virus, zucchini yellow mosaic virus or watermelon mosaic virus 2.

* * * * *

UNITED STATES PATENT AND TRADEMARK OFFICE
CERTIFICATE OF CORRECTION

PATENT NO.: 6,046,384

DATED : April 4, 2000

INVENTOR(S): McMaster *et al.*

It is hereby certified that error appear(s) in the above-identified patent and that said Letters Patent are hereby corrected as shown below:

On the cover sheet under "Other Publications" first reference, "Wang C.H. et al.," please delete "The American Phytopathologial Society" and insert -- Phytopathology--.

In Column 1, line 7, please delete "Dec. 30, 1995" and insert -- Dec. 30, 1994--.

Signed and Sealed this

Twenty-second Day of May, 2001

*Attest:*

NICHOLAS P. GODICI

*Attesting Officer*     *Acting Director of the United States Patent and Trademark Office*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 1789 base pairs
      (B) TYPE: nucleic acid
      (C) STRANDEDNESS: Not Relevant
      (D) TOPOLOGY: Not Relevant (ii) MOLECULE TYPE: DNA (genomic)

(ix) FEATURE:
      (A) NAME/KEY: CDS
      (B) LOCATION: 3..1779

(xi) SEQUENCE DESCRIPTION: SEQ ID NO:1:

```
CC ATG GGC TTC TCT CTC CTT GGT ATC ATA AAC ACT ATC CAG AGT AGA          47
   Met Gly Phe Ser Leu Leu Gly Ile Ile Asn Thr Ile Gln Ser Arg
    1               5                  10                  15

TAT TTA GTT GAT CAT TCA GTT GAG AAT ATC AGA AAG CTT CAA CTA GCG         95
Tyr Leu Val Asp His Ser Val Glu Asn Ile Arg Lys Leu Gln Leu Ala
                20                  25                  30

AAG GCC CAG ATT CAA CAA CTT GAA GCT CAT GTG CAA GAG AAC AAT GTT        143
```

```
Lys Ala Gln Ile Gln Gln Leu Glu Ala His Val Gln Glu Asn Asn Val
             35                  40                  45

GGA AAT TTA ATT CAA TCT CTT GGT GCT GTC AGA GCT GTT TAT CAT CAA        191
Gly Asn Leu Ile Gln Ser Leu Gly Ala Val Arg Ala Val Tyr His Gln
         50                  55                  60

GGT GTT GAT GGA GTC AAG CAC ATA AAG CGA GAG TTG GGC TTG AAA GGA        239
Gly Val Asp Gly Val Lys His Ile Lys Arg Glu Leu Gly Leu Lys Gly
 65                  70                  75

GTT TGG GAT GGT TCA TTA ATG ATC AAG GAT CGA ATT GTA TGC GGT TTC        287
Val Trp Asp Gly Ser Leu Met Ile Lys Asp Arg Ile Val Cys Gly Phe
 80                  85                  90                  95

ACA ATG GCT GGT GGT GCA ATG CTC TTG TAC CAA CAC TTT CGT GAT AAG        335
Thr Met Ala Gly Gly Ala Met Leu Leu Tyr Gln His Phe Arg Asp Lys
                100                 105                 110

CTT ACA AAT GTA CAT GTG TTT CAC CAA GGT TTC TCT GCG CGA CAA CGA        383
Leu Thr Asn Val His Val Phe His Gln Gly Phe Ser Ala Arg Gln Arg
             115                 120                 125

CAA AAG TTA CGA TTT AAG TCA GCA GCA AAT GCT AAG CTT GGT CGA GAA        431
Gln Lys Leu Arg Phe Lys Ser Ala Ala Asn Ala Lys Leu Gly Arg Glu
         130                 135                 140

GTC TAT GGA GAT GAC GGG ACA ATT GAG CAC TAT TTC GGA GAA GCA TAC        479
Val Tyr Gly Asp Asp Gly Thr Ile Glu His Tyr Phe Gly Glu Ala Tyr
145                 150                 155

ACA AAG AAA GGA AAC AAG AAG GGA AAG ATG CAT GGC ATG GGT GTT AAA        527
Thr Lys Lys Gly Asn Lys Lys Gly Lys Met His Gly Met Gly Val Lys
160                 165                 170                 175

ACG AGA AAG TTC GTT GCA ACA TAT GGA TTT AAA CCA GAG GAT TAT TCA        575
Thr Arg Lys Phe Val Ala Thr Tyr Gly Phe Lys Pro Glu Asp Tyr Ser
                180                 185                 190

TAC GTG CGG TAC TTG GAT CCT TTA ACA GGT GAG ACT TTG GAT GAA AGC        623
Tyr Val Arg Tyr Leu Asp Pro Leu Thr Gly Glu Thr Leu Asp Glu Ser
             195                 200                 205

CCA CAG ACT GAC ATC TCA ATG GTG CAA GAA CAT TTT GGT GAT ATT CGG        671
Pro Gln Thr Asp Ile Ser Met Val Gln Glu His Phe Gly Asp Ile Arg
         210                 215                 220

AGT AAA TAT TTG GAT TCA GAC AGC TTC GAC AGG CAG GCT TTA ATA GCA        719
Ser Lys Tyr Leu Asp Ser Asp Ser Phe Asp Arg Gln Ala Leu Ile Ala
225                 230                 235

AAC AAT ACA ATT AAG GCC TAT TAT GTC CGA AAC TCC GCG AAG ACA GCA        767
Asn Asn Thr Ile Lys Ala Tyr Tyr Val Arg Asn Ser Ala Lys Thr Ala
240                 245                 250                 255

TTG GAA GTC GAT TTG ACA CCG CAT AAC CCT CTG AAA GTT TGT GAC AAC        815
Leu Glu Val Asp Leu Thr Pro His Asn Pro Leu Lys Val Cys Asp Asn
                260                 265                 270

AAA TTG ACT ATT GCA GGA TTT CCT GAT AGA GAA GCT GAA CTG AGA CAA        863
Lys Leu Thr Ile Ala Gly Phe Pro Asp Arg Glu Ala Glu Leu Arg Gln
             275                 280                 285

ACA GGC CCA GCC AGA ACT ATT CAA GCC GAT CAA GTT CCA CCA CCT TCG        911
Thr Gly Pro Ala Arg Thr Ile Gln Ala Asp Gln Val Pro Pro Pro Ser
         290                 295                 300

AAA TCA GTT CAT CAC GAA GGA AAA AGT CTT TGT CAA GGT ATG AGA AAT        959
Lys Ser Val His His Glu Gly Lys Ser Leu Cys Gln Gly Met Arg Asn
305                 310                 315

TAC AAT GGC ATA GCT TCC GTG GTT TGC CAT TTG AAA AAC ACA TCG GGA       1007
Tyr Asn Gly Ile Ala Ser Val Val Cys His Leu Lys Asn Thr Ser Gly
320                 325                 330                 335

GAT GGG AGA AGC CTA TTT GGA ATC GGA TAT AAC TCG TTC ATC ATT ACA       1055
Asp Gly Arg Ser Leu Phe Gly Ile Gly Tyr Asn Ser Phe Ile Ile Thr
                340                 345                 350
```

```
AAC CGA CAT TTG TTC AAA GAA AAT AAT GGT GAA CTT ATA GTG AAA TCC        1103
Asn Arg His Leu Phe Lys Glu Asn Asn Gly Glu Leu Ile Val Lys Ser
            355                 360                 365

CAA CAC GGC AAG TTT GTT GTC AAG AAC ACC TCA ACG CTC CGA ATT GCT        1151
Gln His Gly Lys Phe Val Val Lys Asn Thr Ser Thr Leu Arg Ile Ala
        370                 375                 380

CCA GTT GGA AAA ACT GAT CTT TTG ATA ATT CGG ATG CCG AAA GAC TTT        1199
Pro Val Gly Lys Thr Asp Leu Leu Ile Ile Arg Met Pro Lys Asp Phe
385                 390                 395

CCT CCA TTC CAT AGT AGA GCT AGG TTT AGG GCC ATG AAA GCT GGA GAC        1247
Pro Pro Phe His Ser Arg Ala Arg Phe Arg Ala Met Lys Ala Gly Asp
400                 405                 410                 415

AAG GTT TGC ATG ATC GGT GTT GAC TAC CAA GAG AAT CAT ATT GCG AGC        1295
Lys Val Cys Met Ile Gly Val Asp Tyr Gln Glu Asn His Ile Ala Ser
                420                 425                 430

AAA GTA TCT GAA ACT TCT ATT ATC AGT GAG GGC ACG GGA GAG TTT GGA        1343
Lys Val Ser Glu Thr Ser Ile Ile Ser Glu Gly Thr Gly Glu Phe Gly
            435                 440                 445

TGC CAT TGG ATA TCC ACG AAT GAT GGT GAT TGC GGT AAT CCA CTA GTT        1391
Cys His Trp Ile Ser Thr Asn Asp Gly Asp Cys Gly Asn Pro Leu Val
        450                 455                 460

AGT GTT TCA GAT GGT TTC ATT GTT GGC TTG CAT AGT TTG TCG ACA TCA        1439
Ser Val Ser Asp Gly Phe Ile Val Gly Leu His Ser Leu Ser Thr Ser
465                 470                 475

ACC GGA AAT CAA AAT TTC TTC GCT AAA ATA CCC GCA CAA TTT GAA GAA        1487
Thr Gly Asn Gln Asn Phe Phe Ala Lys Ile Pro Ala Gln Phe Glu Glu
480                 485                 490                 495

AAG GTC CTG AGG AAA ATT GAT GAA TTA ACA TGG AGC AAA CAC TGG AGC        1535
Lys Val Leu Arg Lys Ile Asp Glu Leu Thr Trp Ser Lys His Trp Ser
                500                 505                 510

TAC AAT ATT AAT GAA CTG AGT TGG GGA GCT CTT AAG GTG TGG GAA AGT        1583
Tyr Asn Ile Asn Glu Leu Ser Trp Gly Ala Leu Lys Val Trp Glu Ser
            515                 520                 525

CGT CCC GAA GCA ATT TTT AAT GCG CAA AAG GAA GTC AAC CAA TTG AAT        1631
Arg Pro Glu Ala Ile Phe Asn Ala Gln Lys Glu Val Asn Gln Leu Asn
        530                 535                 540

GTT TTT GAG CAA AGT GGT AGT CGT TGG CTC TTC GAC AAA TTA CAC GGC        1679
Val Phe Glu Gln Ser Gly Ser Arg Trp Leu Phe Asp Lys Leu His Gly
545                 550                 555

AAT TTG AAG GGT GTA AGT TCC GCT TCT AGC AAT TTG GTG ACA AAG CAC        1727
Asn Leu Lys Gly Val Ser Ser Ala Ser Ser Asn Leu Val Thr Lys His
560                 565                 570                 575

GTT GTT AAA GGC ATT TGT CCT CTC TTC AGG AAC TAT CTC GAG TGT GAT        1775
Val Val Lys Gly Ile Cys Pro Leu Phe Arg Asn Tyr Leu Glu Cys Asp
                580                 585                 590

GAA   T AGGCCCATGG                                                     1789
Glu (2) INFORMATION FOR SEQ ID NO:2:

(i) SEQUENCE CHARACTERISTICS:
        (A) LENGTH: 592 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Phe Ser Leu Leu Gly Ile Ile Asn Thr Ile Gln Ser Arg Tyr
1               5                   10                  15

Leu Val Asp His Ser Val Glu Asn Ile Arg Lys Leu Gln Leu Ala Lys
```

-continued

```
                20                  25                  30
Ala Gln Ile Gln Gln Leu Glu Ala His Val Gln Glu Asn Asn Val Gly
             35                  40                  45
Asn Leu Ile Gln Ser Leu Gly Ala Val Arg Ala Val Tyr His Gln Gly
 50                  55                  60
Val Asp Gly Val Lys His Ile Lys Arg Glu Leu Gly Leu Lys Gly Val
 65                  70                  75                  80
Trp Asp Gly Ser Leu Met Ile Lys Asp Arg Ile Val Cys Gly Phe Thr
                 85                  90                  95
Met Ala Gly Gly Ala Met Leu Leu Tyr Gln His Phe Arg Asp Lys Leu
                100                 105                 110
Thr Asn Val His Val Phe His Gln Gly Phe Ser Ala Arg Gln Arg Gln
            115                 120                 125
Lys Leu Arg Phe Lys Ser Ala Ala Asn Ala Lys Leu Gly Arg Glu Val
       130                 135                 140
Tyr Gly Asp Asp Gly Thr Ile Glu His Tyr Phe Gly Glu Ala Tyr Thr
145                 150                 155                 160
Lys Lys Gly Asn Lys Lys Gly Lys Met His Gly Met Gly Val Lys Thr
                165                 170                 175
Arg Lys Phe Val Ala Thr Tyr Gly Phe Lys Pro Glu Asp Tyr Ser Tyr
            180                 185                 190
Val Arg Tyr Leu Asp Pro Leu Thr Gly Glu Thr Leu Asp Glu Ser Pro
       195                 200                 205
Gln Thr Asp Ile Ser Met Val Gln Glu His Phe Gly Asp Ile Arg Ser
       210                 215                 220
Lys Tyr Leu Asp Ser Asp Ser Phe Asp Arg Gln Ala Leu Ile Ala Asn
225                 230                 235                 240
Asn Thr Ile Lys Ala Tyr Tyr Val Arg Asn Ser Ala Lys Thr Ala Leu
                245                 250                 255
Glu Val Asp Leu Thr Pro His Asn Pro Leu Lys Val Cys Asp Asn Lys
            260                 265                 270
Leu Thr Ile Ala Gly Phe Pro Asp Arg Glu Ala Glu Leu Arg Gln Thr
       275                 280                 285
Gly Pro Ala Arg Thr Ile Gln Ala Asp Gln Val Pro Pro Ser Lys
       290                 295                 300
Ser Val His His Glu Gly Lys Ser Leu Cys Gln Gly Met Arg Asn Tyr
305                 310                 315                 320
Asn Gly Ile Ala Ser Val Cys His Leu Lys Asn Thr Ser Gly Asp
                325                 330                 335
Gly Arg Ser Leu Phe Gly Ile Gly Tyr Asn Ser Phe Ile Ile Thr Asn
            340                 345                 350
Arg His Leu Phe Lys Glu Asn Asn Gly Glu Leu Ile Val Lys Ser Gln
       355                 360                 365
His Gly Lys Phe Val Val Lys Asn Thr Ser Thr Leu Arg Ile Ala Pro
       370                 375                 380
Val Gly Lys Thr Asp Leu Leu Ile Ile Arg Met Pro Lys Asp Phe Pro
385                 390                 395                 400
Pro Phe His Ser Arg Ala Arg Phe Arg Ala Met Lys Ala Gly Asp Lys
                405                 410                 415
Val Cys Met Ile Gly Val Asp Tyr Gln Glu Asn His Ile Ala Ser Lys
            420                 425                 430
Val Ser Glu Thr Ser Ile Ile Ser Glu Gly Thr Gly Glu Phe Gly Cys
       435                 440                 445
```

```
His Trp Ile Ser Thr Asn Asp Gly Asp Cys Gly Asn Pro Leu Val Ser
    450                 455                 460

Val Ser Asp Gly Phe Ile Val Gly Leu His Ser Leu Ser Thr Ser Thr
465                 470                 475                 480

Gly Asn Gln Asn Phe Phe Ala Lys Ile Pro Ala Gln Phe Glu Glu Lys
                485                 490                 495

Val Leu Arg Lys Ile Asp Glu Leu Thr Trp Ser Lys His Trp Ser Tyr
            500                 505                 510

Asn Ile Asn Glu Leu Ser Trp Gly Ala Leu Lys Val Trp Glu Ser Arg
        515                 520                 525

Pro Glu Ala Ile Phe Asn Ala Gln Lys Glu Val Asn Gln Leu Asn Val
    530                 535                 540

Phe Glu Gln Ser Gly Ser Arg Trp Leu Phe Asp Lys Leu His Gly Asn
545                 550                 555                 560

Leu Lys Gly Val Ser Ser Ala Ser Ser Asn Leu Val Thr Lys His Val
                565                 570                 575

Val Lys Gly Ile Cys Pro Leu Phe Arg Asn Tyr Leu Glu Cys Asp Glu
            580                 585                 590

(2) INFORMATION FOR SEQ ID NO:3:

(i) SEQUENCE CHARACTERISTICS:
        (A) LENGTH: 44 base pairs
        (B) TYPE: nucleic acid
        (C) STRANDEDNESS: Not Relevant
        (D) TOPOLOGY: Not Relevant (ii) MOLECULE TYPE: DNA (genomic)

(xi) SEQUENCE DESCRIPTION: SEQ ID NO:3:

GCTATGACAG GAATTCACTG GCCTAACCAT GGGCTTCTCT CTCC                    44

(2) INFORMATION FOR SEQ ID NO:4:

(i) SEQUENCE CHARACTERISTICS:
        (A) LENGTH: 42 base pairs
        (B) TYPE: nucleic acid
        (C) STRANDEDNESS: Not Relevant
        (D) TOPOLOGY: Not Relevant (ii) MOLECULE TYPE: DNA (genomic)

(xi) SEQUENCE DESCRIPTION: SEQ ID NO:4:

CACACTACTT ATCCGGGTAC CAAAGAACCT AGGTGAATAC CC                      42

(2) INFORMATION FOR SEQ ID NO:5:

(i) SEQUENCE CHARACTERISTICS:
        (A) LENGTH: 1797 base pairs
        (B) TYPE: nucleic acid
        (C) STRANDEDNESS: Not Relevant
        (D) TOPOLOGY: Not Relevant (ii) MOLECULE TYPE: DNA (genomic)

(ix) FEATURE:
        (A) NAME/KEY: CDS
        (B) LOCATION: 3..1779

(ix) FEATURE:
        (A) NAME/KEY: CDS
        (B) LOCATION: 1782..1797

(xi) SEQUENCE DESCRIPTION: SEQ ID NO:5:
```

```
CC ATG GGC TTC TCT CTC CTT GGT GTT ATA AAC ACT ATC CAG AGT AGA            47
   Met Gly Phe Ser Leu Leu Gly Val Ile Asn Thr Ile Gln Ser Arg
    1               5                  10                  15

TAT CTA GTT GAC CAC TCA GTT GAA AAT ATC AGA AAA CTT CAA CTG GCG            95
Tyr Leu Val Asp His Ser Val Glu Asn Ile Arg Lys Leu Gln Leu Ala
                 20                  25                  30

AAG GCC CAA ATT CAA CAA CTT GAA GCT CAT GTG CAG GAA AAC AAT GTT           143
Lys Ala Gln Ile Gln Gln Leu Glu Ala His Val Gln Glu Asn Asn Val
             35                  40                  45

GAA AAT TTA ATT CAA TCT CTT GGT GCT GTC AGA GCT GTT TAC CAT CAA           191
Glu Asn Leu Ile Gln Ser Leu Gly Ala Val Arg Ala Val Tyr His Gln
         50                  55                  60

AGT GTT GAT GGA TTT AAA CAC ATA AAG CGA GAG TTG GGT TTG AAA GGA           239
Ser Val Asp Gly Phe Lys His Ile Lys Arg Glu Leu Gly Leu Lys Gly
     65                  70                  75

GTT TGG GAT GGC TCA TTG ATG ATT AAG GAT GCG ATT GTA TGC GGT TTC           287
Val Trp Asp Gly Ser Leu Met Ile Lys Asp Ala Ile Val Cys Gly Phe
 80                  85                  90                  95

ACA ATG GCT GGC GGT GCG ATG CTT TTG TAC CAA CAT TTT CGT GAT AAG           335
Thr Met Ala Gly Gly Ala Met Leu Leu Tyr Gln His Phe Arg Asp Lys
                100                 105                 110

TTT ACA AAT GTT CAT GTG TTT CAC CAA GGT TTC TCT GCG CGA CAG AGA           383
Phe Thr Asn Val His Val Phe His Gln Gly Phe Ser Ala Arg Gln Arg
             115                 120                 125

CAA AAG TTA AGA TTT AAG TCA GCA GCG AAT GCT AAG CTT GGT CGA GAG           431
Gln Lys Leu Arg Phe Lys Ser Ala Ala Asn Ala Lys Leu Gly Arg Glu
         130                 135                 140

GTC TAT GGA GAT GAT GGG ACA ATT GAG CAC TAT TTT GGA GAA GCG TAC           479
Val Tyr Gly Asp Asp Gly Thr Ile Glu His Tyr Phe Gly Glu Ala Tyr
     145                 150                 155

ACG AAG AAA GGA AAC AAG AAA GGA AAG ATG CAT GGC ATG GGT GTT AAG           527
Thr Lys Lys Gly Asn Lys Lys Gly Lys Met His Gly Met Gly Val Lys
160                 165                 170                 175

ACG AGA AAG TTT GTT GCG ACA TAT GGA TTT AAA CCG GAG GAT TAC TCG           575
Thr Arg Lys Phe Val Ala Thr Tyr Gly Phe Lys Pro Glu Asp Tyr Ser
                180                 185                 190

TAC GTG CGG TAC TTG GAC CCT TTA ACA GGT GAG ACT TTG GAT GAA AGC           623
Tyr Val Arg Tyr Leu Asp Pro Leu Thr Gly Glu Thr Leu Asp Glu Ser
             195                 200                 205

CCA CAG ACT GAT ATC TCA ATG GTG CAA GAT CAT TTT AGT GAT ATT CGG           671
Pro Gln Thr Asp Ile Ser Met Val Gln Asp His Phe Ser Asp Ile Arg
         210                 215                 220

AGA AAG TAC ATG GAT TCA GAC AGC TTC GAT AGG CAG GCT TTA ATA GCA           719
Arg Lys Tyr Met Asp Ser Asp Ser Phe Asp Arg Gln Ala Leu Ile Ala
     225                 230                 235

AAC AAT ACA ATT AAG GCT TAT TAT GTC CGA AAC TCC GCG AAG GCA GCA           767
Asn Asn Thr Ile Lys Ala Tyr Tyr Val Arg Asn Ser Ala Lys Ala Ala
240                 245                 250                 255

TTG GAA GTC GAT CTG ACA CCG CAC AAC CCT CTC AAA GTT TGT GAC AAT           815
Leu Glu Val Asp Leu Thr Pro His Asn Pro Leu Lys Val Cys Asp Asn
                260                 265                 270

AAA TTG ACC ATT GCA GGA TTT CCT GAC AGG GAA GCT GAG CTG AGA CAA           863
Lys Leu Thr Ile Ala Gly Phe Pro Asp Arg Glu Ala Glu Leu Arg Gln
             275                 280                 285

ACA GGC CCG CCC AGA ACT ATT CAA GTA GAT CAA GTG CCA CCA CCC TCG           911
Thr Gly Pro Pro Arg Thr Ile Gln Val Asp Gln Val Pro Pro Pro Ser
         290                 295                 300

AAA TCA GTT CAT CAC GAA GGA AAA AGT CTT TGT CAA GGC ATG AGA AAT           959
Lys Ser Val His His Glu Gly Lys Ser Leu Cys Gln Gly Met Arg Asn
     305                 310                 315
```

-continued

| | |
|---|---|
| TAC AAT GGC ATA GCT TCT GTG GTT TGC CAT TTG AAA AAC ACA TCA GGA<br>Tyr Asn Gly Ile Ala Ser Val Val Cys His Leu Lys Asn Thr Ser Gly<br>320     325     330     335 | 1007 |
| AAG GGA AAG AGC TTG TTT GGA ATT GGA TAT AAT TCA TTC ATC ATT ACC<br>Lys Gly Lys Ser Leu Phe Gly Ile Gly Tyr Asn Ser Phe Ile Ile Thr<br>     340     345     350 | 1055 |
| AAC CGA CAT TTG TTC AAG GAG AAT AAT GGT GAA CTT ATA GTG AAA TCC<br>Asn Arg His Leu Phe Lys Glu Asn Asn Gly Glu Leu Ile Val Lys Ser<br>     355     360     365 | 1103 |
| CAA CAC GGT AAG TTT ATT GTC AAG AAC ACC ACA ACA CTC CGA ATT GCT<br>Gln His Gly Lys Phe Ile Val Lys Asn Thr Thr Thr Leu Arg Ile Ala<br>   370     375     380 | 1151 |
| CCA GTT GGA AAG ACT GAT CTT TTA ATT ATT CGG ATG CCG AAA GAT TTT<br>Pro Val Gly Lys Thr Asp Leu Leu Ile Ile Arg Met Pro Lys Asp Phe<br>385     390     395 | 1199 |
| CCT CCA TTC CAT AGC AGA GCT AGG TTT AGG GCC ATG AAA GCT GGG GAC<br>Pro Pro Phe His Ser Arg Ala Arg Phe Arg Ala Met Lys Ala Gly Asp<br>400     405     410     415 | 1247 |
| AAG GTT TGC ATG ATA GGT GTT GAC TAC CAA GAG AAT CAT ATC GCG AGC<br>Lys Val Cys Met Ile Gly Val Asp Tyr Gln Glu Asn His Ile Ala Ser<br>     420     425     430 | 1295 |
| AAA GTA TCT GAA ACC TCT ATC ATC AGT GAG GGC ACG GGA GAT TTT GGA<br>Lys Val Ser Glu Thr Ser Ile Ile Ser Glu Gly Thr Gly Asp Phe Gly<br>   435     440     445 | 1343 |
| TGC CAC TGG ATA TCC ACG AAT GAC GGT GAT TGC GGT AAT CCT TTA GTT<br>Cys His Trp Ile Ser Thr Asn Asp Gly Asp Cys Gly Asn Pro Leu Val<br>   450     455     460 | 1391 |
| AGT GTT TCA GAT GGT TTT ATT GTC GGC TTG CAT AGT TTG TCG ACA TCA<br>Ser Val Ser Asp Gly Phe Ile Val Gly Leu His Ser Leu Ser Thr Ser<br>465     470     475 | 1439 |
| ACT GGA GAT CAA AAT TTC TTT GCT AAA ATA CCC GCA CAA TTT GAA GAA<br>Thr Gly Asp Gln Asn Phe Phe Ala Lys Ile Pro Ala Gln Phe Glu Glu<br>480     485     490     495 | 1487 |
| AAG GTC CTT AGG AAG ATT GAT GAT TTA ACT TGG AGC AAA CAC TGG AGC<br>Lys Val Leu Arg Lys Ile Asp Asp Leu Thr Trp Ser Lys His Trp Ser<br>     500     505     510 | 1535 |
| TAT AAT ATT AAT GAA CTG AGT TGG GGA GCT CTC AAA GTG TGG GAA AGT<br>Tyr Asn Ile Asn Glu Leu Ser Trp Gly Ala Leu Lys Val Trp Glu Ser<br>   515     520     525 | 1583 |
| CGG CCC GAA GCA ATT TTT AAC GCG CAA AAG GAA GTT AAT CAA TTG AAT<br>Arg Pro Glu Ala Ile Phe Asn Ala Gln Lys Glu Val Asn Gln Leu Asn<br>   530     535     540 | 1631 |
| GTT TTC GAG CAA AGT GGT AGT CGT TGG CTC TTT GAC AAA TTA CAC GGC<br>Val Phe Glu Gln Ser Gly Ser Arg Trp Leu Phe Asp Lys Leu His Gly<br>545     550     555 | 1679 |
| AAT TTG AAA GGA GTT AGC TCC GCT CCT AGC AAT TTG GTG ACA AAG CAC<br>Asn Leu Lys Gly Val Ser Ser Ala Pro Ser Asn Leu Val Thr Lys His<br>560     565     570     575 | 1727 |
| GTT GTT AAA GGA ATT TGT CCT CTT TTC AGG AAC TAT CTC GAG TGT GAT<br>Val Val Lys Gly Ile Cys Pro Leu Phe Arg Asn Tyr Leu Glu Cys Asp<br>     580     585     590 | 1775 |
| GAA T AG GCC CAT GGT TGC GCT G<br>Glu   Ala His Gly Cys Ala<br>     1     5 | 1797 |

(2) INFORMATION FOR SEQ ID NO:6:

(i) SEQUENCE CHARACTERISTICS:
    (A) LENGTH: 592 amino acids
    (B) TYPE: amino acid (D) TOPOLOGY: linear (ii) MOLECULE TYPE: protein (xi) SEQUENCE DESCRIPTION: SEQ ID NO:6:

```
Met Gly Phe Ser Leu Leu Gly Val Ile Asn Thr Ile Gln Ser Arg Tyr
  1               5                  10                  15

Leu Val Asp His Ser Val Glu Asn Ile Arg Lys Leu Gln Leu Ala Lys
             20                  25                  30

Ala Gln Ile Gln Gln Leu Glu Ala His Val Gln Glu Asn Asn Val Glu
         35                  40                  45

Asn Leu Ile Gln Ser Leu Gly Ala Val Arg Ala Val Tyr His Gln Ser
     50                  55                  60

Val Asp Gly Phe Lys His Ile Lys Arg Glu Leu Gly Leu Lys Gly Val
 65                  70                  75                  80

Trp Asp Gly Ser Leu Met Ile Lys Asp Ala Ile Val Cys Gly Phe Thr
                 85                  90                  95

Met Ala Gly Gly Ala Met Leu Leu Tyr Gln His Phe Arg Asp Lys Phe
             100                 105                 110

Thr Asn Val His Val Phe His Gln Gly Phe Ser Ala Arg Gln Arg Gln
         115                 120                 125

Lys Leu Arg Phe Lys Ser Ala Ala Asn Ala Lys Leu Gly Arg Glu Val
    130                 135                 140

Tyr Gly Asp Asp Gly Thr Ile Glu His Tyr Phe Gly Glu Ala Tyr Thr
145                 150                 155                 160

Lys Lys Gly Asn Lys Lys Gly Lys Met His Gly Met Gly Val Lys Thr
                165                 170                 175

Arg Lys Phe Val Ala Thr Tyr Gly Phe Lys Pro Glu Asp Tyr Ser Tyr
            180                 185                 190

Val Arg Tyr Leu Asp Pro Leu Thr Gly Glu Thr Leu Asp Glu Ser Pro
        195                 200                 205

Gln Thr Asp Ile Ser Met Val Gln Asp His Phe Ser Asp Ile Arg Arg
    210                 215                 220

Lys Tyr Met Asp Ser Asp Ser Phe Asp Arg Gln Ala Leu Ile Ala Asn
225                 230                 235                 240

Asn Thr Ile Lys Ala Tyr Tyr Val Arg Asn Ser Ala Lys Ala Ala Leu
                245                 250                 255

Glu Val Asp Leu Thr Pro His Asn Pro Leu Lys Val Cys Asp Asn Lys
            260                 265                 270

Leu Thr Ile Ala Gly Phe Pro Asp Arg Glu Ala Glu Leu Arg Gln Thr
        275                 280                 285

Gly Pro Pro Arg Thr Ile Gln Val Asp Gln Val Pro Pro Ser Lys
    290                 295                 300

Ser Val His His Glu Gly Lys Ser Leu Cys Gln Gly Met Arg Asn Tyr
305                 310                 315                 320

Asn Gly Ile Ala Ser Val Val Cys His Leu Lys Asn Thr Ser Gly Lys
                325                 330                 335

Gly Lys Ser Leu Phe Gly Ile Gly Tyr Asn Ser Phe Ile Ile Thr Asn
            340                 345                 350

Arg His Leu Phe Lys Glu Asn Asn Gly Glu Leu Ile Val Lys Ser Gln
        355                 360                 365

His Gly Lys Phe Ile Val Lys Asn Thr Thr Thr Leu Arg Ile Ala Pro
    370                 375                 380

Val Gly Lys Thr Asp Leu Leu Ile Ile Arg Met Pro Lys Asp Phe Pro
```

```
                                            385                 390                 395                 400

Pro Phe His Ser Arg Ala Arg Phe Arg Ala Met Lys Ala Gly Asp Lys
                                            405                 410                 415

Val Cys Met Ile Gly Val Asp Tyr Gln Glu Asn His Ile Ala Ser Lys
                                            420                 425                 430

Val Ser Glu Thr Ser Ile Ile Ser Glu Gly Thr Gly Asp Phe Gly Cys
                                            435                 440                 445

His Trp Ile Ser Thr Asn Asp Gly Asp Cys Gly Asn Pro Leu Val Ser
                                            450                 455                 460

Val Ser Asp Gly Phe Ile Val Gly Leu His Ser Leu Ser Thr Ser Thr
                            465                 470                 475                 480

Gly Asp Gln Asn Phe Phe Ala Lys Ile Pro Ala Gln Phe Glu Glu Lys
                                            485                 490                 495

Val Leu Arg Lys Ile Asp Asp Leu Thr Trp Ser Lys His Trp Ser Tyr
                                            500                 505                 510

Asn Ile Asn Glu Leu Ser Trp Gly Ala Leu Lys Val Trp Glu Ser Arg
                                            515                 520                 525

Pro Glu Ala Ile Phe Asn Ala Gln Lys Glu Val Asn Gln Leu Asn Val
                                            530                 535                 540

Phe Glu Gln Ser Gly Ser Arg Trp Leu Phe Asp Lys Leu His Gly Asn
                            545                 550                 555                 560

Leu Lys Gly Val Ser Ser Ala Pro Ser Asn Leu Val Thr Lys His Val
                                            565                 570                 575

Val Lys Gly Ile Cys Pro Leu Phe Arg Asn Tyr Leu Glu Cys Asp Glu
                                            580                 585                 590

(2) INFORMATION FOR SEQ ID NO:7:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO:7:

Ala His Gly Cys Ala
 1               5

(2) INFORMATION FOR SEQ ID NO:8:

(i) SEQUENCE CHARACTERISTICS:
        (A) LENGTH: 1900 base pairs
        (B) TYPE: nucleic acid
        (C) STRANDEDNESS: Not Relevant
        (D) TOPOLOGY: Not Relevant (ii) MOLECULE TYPE: DNA (genomic)

(xi) SEQUENCE DESCRIPTION: SEQ ID NO:8:

GCACTGGCCT AAACTCTAGC TTCTCTCTCC TTGGTGTTAT AAACACTATC CAGAGTAGAT      60

ATCTAGTTGA CCACTCAGTT GAAAATATCA GAAAACTTCA ACTGGCAAAG GCCCAGATTC     120

AACAACTTGA AGCTCACATG CAGGAAAACA ATGTTGAAAA TTTAATTCAA TCTCTTGGTG     180

CTGTAAGAGC TGTTTACCAT CAAAGTGTTG ATGGATTTAA ACACATAAAG CGAGAGTTGG     240

GTTTGAAAGG AGTTTGGGAT GGCTCATTGA TGATTAAGGA TGCGATTGTA TGCGGTTTCA     300

CAATGGCTGG CGGTGCGATG CTTTTGTACC AACACTTTCG TGATAAGTTT ACAAATGTTC     360

ATGTGTTTCA CCAAGGTTTC TCTGCGCGAC AGAGACAAAA GTTAAGATTT AAGTCAGCAG     420
```

-continued

```
CGAATGCTAA GCTTGGTCGA GAGGTCTATG GAGATGATGG GACAATTGAG CACTATTTTG     480

GAGAAGCGTA CACGAAGAAA GGAAACAAGA AAGGAAAGAT GCATGGCATG GGTGTTAAGA     540

CGAGAAAGTT TGTTGCGACA TATGGATTTA AACCGGAGGA TTACTCGTAC GTGCGGTACT     600

TGGACCCTTT AACAGGTGAG ACTTTGGATG AAAGCCCACA GACTGATATC TCAATGGTGC     660

AAGATCATTT TAGTGATATT CGGAGAAAGT ACATGGATTC AGACAGCTTC GATAGGCAGG     720

CTTTAATAGC AAACAATACA ATTAAGGCTT ATTATGTCCG AAACTCCGCG AAGGCAGCAT     780

TGGAAGTCGA TCTGACACCG CACAACCCTC TCAAAGTTTG TGACAATAAA TTGACCATTG     840

CAGGATTTCC TGACAGGGAA GCTGAGCTAA GACAAACAGG CCCGCCCAGA ACTATTCAAG     900

TAGATCAAGT GCCACCACCC TCGAAATCAG TTCATCACGA AGGAAAAAGT CTTTGTCAAG     960

GCATGAGAAA TTACAATGGC ATAGCTTCTG TGGTTTGCCA TTTGAAAAAC ACATCAGGAA    1020

AGGGAAGAG CTTGTTTGGA ATTGGATATA ATTCATTCAT CATTACCAAC CGACATTTGT    1080

TCAAGGAGAA TAATGGTGAA CTTATAGTGA AATCCCAACA CGGTAAGTTT ATTGTCAAGA    1140

ACACCACAAC ACTCCAAATT GCTCCAGTTG GAAAGACTGA TCTTTTAATT ATTCGGATGC    1200

CGAAAGATTT TCCTCCATTC CATAGCAGAG CTAGGTTTAG GGCCATGAAA GCTGGGGACA    1260

AGGTTTGCAT GATAGGTGTT GACTACCAAG AGAATCATAT CGCGAGCAAA GTATCTGAAA    1320

CCTCTATCAT CAGTGAGGGC ACGGGAGATT TTGGATGCCA CTGGATATCC ACGAATGACG    1380

GTGATTGCGG TAATCCTTTA GTTAGTGTTT CAGATGGTTT TATTGTCGGC TTGCATAGTT    1440

TGTCGACATC AACTGGAGAT CAAAATTTCT TGCCAAAAT ACCCGCACAA TTTGAAGAAA    1500

AGGTCCTTAG GAAGATTGAT GATTTAACTT GGAGCAAACA CTGGAGCTAT AATATTAATG    1560

AACTGAGTTG GGGAGCTCTC AAAGTGTGGG AAAGTCGGCC CGAAGCAATT TTTAACGCAC    1620

AAAAGGAAGT TAATCAATTG AATGTTTTCG AGCAAAGTGG TGGTCGTTGG CTCTTTGACA    1680

AATTACACGG CAATTTGAAA GGAGTTAGCT CCGCTCCTAG CAATTTGGTG ACAAAGCACG    1740

TTGTTAAAGG AATTTGTCCT CTTTTCAGGA ACTATCTCGA GTGTGATGAA GAGGCTAAAG    1800

CTTTCTTTAG TCCACTTATG GGTCACTACA TGAAGAGTGT TCTGAGCAAG GAAGCGTACA    1860

TTAAGGATTT ATTGAAATAT TCAAGTGATA TTGTCGTTGG                          1900
```

(2) INFORMATION FOR SEQ ID NO:9:

(i) SEQUENCE CHARACTERISTICS:
        (A) LENGTH: 1900 base pairs
        (B) TYPE: nucleic acid
        (C) STRANDEDNESS: Not Relevant
        (D) TOPOLOGY: Not Relevant (ii) MOLECULE TYPE: DNA (genomic)

(xi) SEQUENCE DESCRIPTION: SEQ ID NO:9:

```
GCACTGGCCT AAACTCTAGC TTCTCTCTCC TTGGTGTTAT AAACACTATC CAGAGTAGAT      60

ATCTAGTTGA CCACTCAGTT GAAAATATCA GAAAACTTCA ACTGGCGAAG GCCCAAATTC     120

AACAACTTGA AGCTCATGTG CAGGAAAACA ATGTTGAAAA TTTAATTCAA TCTCTTGGTG     180

CTGTCAGAGC TGTTTACCAT CAAAGTGTTG ATGGATTTAA ACACATAAAG CGAGAGTTGG     240

CTTTGAAAGG AGTTTGGGAT GGCTCATTGA TGATTAAGGA TGCGATTGTA TGCGGTTTCA     300

CAATGGCTGG CGGTGCGATG CTTTTGTACC AACATTTTCG TGATAAGTTT ACAAATGTTC     360

ATGTGTTTCA CCAAGGTTTC TCTGCGCGAC AGAGACAAAA GTTAAGATTT AAGTCAGCAG     420

CGAATGCTAA GCTTGGTCGA GAGGTCTATG GAGATGATGG GACAATTGAG CACTATTTTG     480
```

```
GAGAAGCGTA CACGAAGAAA GGAAACAAGA AAGGAAAGAT GCATGGCATG GGTGTTAAGA      540

CGAGAAAGTT TGTTGCGACA TATGGATTTA AACCGGAGGA TTACTCGTAC GTGCGGTACT      600

TGGACCCTTT AACAGGTGAG ACTTTGGATG AAAGCCCACA GACTGATATC TCAATGGTGC      660

AAGATCATTT TAGTGATATT CGGAGAAAGT ACATGGATTC AGACAGCTTC GATAGGCAGG      720

CTTTAATAGC AAACAATACA ATTAAGGCTT ATTATGTCCG AAACTCCGCG AAGGCAGCAT      780

TGGAAGTCGA TCTGACACCG CACAACCCTC TCAAAGTTTG TGACAATAAA TTGACCATTG      840

CAGGATTTCC TGACAGGGAA GCTGAGCTGA GACAAACAGG CCCGCCCAGA ACTATTCAAG      900

TAGATCAAGT GCCACCACCC TCGAAATCAG TTCATCACGA AGGAAAAAGT CTTTGTCAAG      960

GCATGAGAAA TTACAATGGC ATAGCTTCTG TGGTTTGCCA TTTGAAAAAC ACATCAGGAA     1020

AGGGAAAGAG CTTGTTTGGA ATTGGATATA ATTCATTCAT CATTACCAAC CGACATTTGT     1080

TCAAGGAGAA TAATGGTGAA CTTATAGTGA AATCCCAACA CGGTAAGTTT ATTGTCAAGA     1140

ACACCACAAC ACTCCGAATT GCTCCAGTTG GAAAGACTGA TCTTTTAATT ATTCGGATGC     1200

CGAAAGATTT TCCTCCATTC CATAGCAGAG CTAGGTTTAG GGCCATGAAA GCTGGGGACA     1260

AGGTTTGCAT GATAGGTGTT GACTACCAAG AGAATCATAT CGCGAGCAAA GTATCTGAAA     1320

CCTCTATCAT CAGTGAGGGC ACGGGAGATT TTGGATGCCA CTGGATATCC ACGAATGACG     1380

GTGATTGCGG TAATCCTTTA GTTAGTGTTT CAGATGGTTT TATTGTCGGC TTGCATAGTT     1440

TGTCGACATC AACTGGAGAT CAAAATTTCT TTGCTAAAAT ACCCGCACAA TTTGAAGAAA     1500

AGGTCCTTAG GAAGATTGAT GATTTAACTT GGAGCAAACA CTGGAGCTAT AATATTAATG     1560

AACTGAGTTG GGGAGCTCTC AAAGTGTGGG AAAGTCGGCC CGAAGCAATT TTTAACGCGC     1620

AAAAGGAAGT TAATCAATTG AATGTTTTCG AGCAAAGTGG TAGTCGTTGG CTCTTTGACA     1680

AATTACACGG CAATTTGAAA GGAGTTAGCT CCGCTCCTAG CAATTTGGTG ACAAAGCACG     1740

TTGTTAAAGG AATTTGTCCT CTTTTCAGGA ACTATCTCGA GTGTGATGAA GAGGCTAAAG     1800

CTTTCTTTAG TCCACTTATG GGTCACTACA TGAAGAGTGT TCTGAGCAAG GAAGCGTACA     1860

TTAAGGATTT ATTGAAATAT TCAAGTGATA TTGTCGTTGG                           1900
```

(2) INFORMATION FOR SEQ ID NO:10:

(i) SEQUENCE CHARACTERISTICS:
        (A) LENGTH: 57 base pairs
        (B) TYPE: nucleic acid
        (C) STRANDEDNESS: Not Relevant
        (D) TOPOLOGY: Not Relevant (ii) MOLECULE TYPE: DNA (genomic)

(xi) SEQUENCE DESCRIPTION: SEQ ID NO:10:

```
TTTACAGAAT TCCCCATGGT AAACATGGTT TCTCTGCGCG ACAGAGACAA AAGTTAA        57
```

(2) INFORMATION FOR SEQ ID NO:11:

(i) SEQUENCE CHARACTERISTICS:
        (A) LENGTH: 39 base pairs
        (B) TYPE: nucleic acid
        (C) STRANDEDNESS: Not Relevant
        (D) TOPOLOGY: Not Relevant (ii) MOLECULE TYPE: DNA (genomic)

(xi) SEQUENCE DESCRIPTION: SEQ ID NO:11:

```
AAGCTCGTTG ATCCAGATGG GTACCCTAGG CTGTTTAAT                            39
```

(2) INFORMATION FOR SEQ ID NO:12:

(i) SEQUENCE CHARACTERISTICS:
        (A) LENGTH: 596 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:12:

```
Ser Ser Phe Ser Leu Leu Gly Val Ile Asn Thr Ile Gln Ser Arg Tyr
1               5                   10                  15

Leu Val Asp His Ser Val Glu Asn Ile Arg Lys Leu Gln Leu Ala Lys
                20                  25                  30

Ala Gln Ile Gln Gln Leu Glu Ala His Val Gln Glu Asn Asn Val Glu
            35                  40                  45

Asn Leu Ile Gln Ser Leu Gly Ala Val Arg Ala Val Tyr His Gln Ser
        50                  55                  60

Val Asp Gly Phe Lys His Ile Lys Arg Glu Leu Gly Leu Lys Gly Val
65                  70                  75                  80

Trp Asp Gly Ser Leu Met Ile Lys Asp Ala Ile Val Cys Gly Phe Thr
                85                  90                  95

Met Ala Gly Gly Ala Met Leu Leu Tyr Gln His Phe Arg Asp Lys Phe
                100                 105                 110

Thr Asn Val His Val Phe His Gln Gly Phe Ser Ala Arg Gln Arg Gln
            115                 120                 125

Lys Leu Arg Phe Lys Ser Ala Ala Asn Ala Lys Leu Gly Arg Glu Val
        130                 135                 140

Tyr Gly Asp Asp Gly Thr Ile Glu His Tyr Phe Gly Glu Ala Tyr Thr
145                 150                 155                 160

Lys Lys Gly Asn Lys Lys Gly Lys Met His Gly Met Gly Val Lys Thr
                165                 170                 175

Arg Lys Phe Val Ala Thr Tyr Gly Phe Lys Pro Glu Asp Tyr Ser Tyr
                180                 185                 190

Val Arg Tyr Leu Asp Pro Leu Thr Gly Glu Thr Leu Asp Glu Ser Pro
            195                 200                 205

Gln Thr Asp Ile Ser Met Val Gln Asp His Phe Ser Asp Ile Arg Arg
        210                 215                 220

Lys Tyr Met Asp Ser Asp Ser Phe Asp Arg Gln Ala Leu Ile Ala Asn
225                 230                 235                 240

Asn Thr Ile Lys Ala Tyr Tyr Val Arg Asn Ser Ala Lys Ala Ala Leu
                245                 250                 255

Glu Val Asp Leu Thr Pro His Asn Pro Leu Lys Val Cys Asp Asn Lys
                260                 265                 270

Leu Thr Ile Ala Gly Phe Pro Asp Arg Glu Ala Glu Leu Arg Gln Thr
            275                 280                 285

Gly Pro Pro Arg Thr Ile Gln Val Asp Gln Val Pro Pro Ser Lys
        290                 295                 300

Ser Val His His Glu Gly Lys Ser Leu Cys Gln Gly Met Arg Asn Tyr
305                 310                 315                 320

Asn Gly Ile Ala Ser Val Val Cys His Leu Lys Asn Thr Ser Gly Lys
                325                 330                 335

Gly Lys Ser Leu Phe Gly Ile Gly Tyr Asn Ser Phe Ile Ile Thr Asn
                340                 345                 350
```

```
Arg His Leu Phe Lys Glu Asn Asn Gly Glu Leu Ile Val Lys Ser Gln
        355                 360                 365

His Gly Lys Phe Ile Val Lys Asn Thr Thr Thr Leu Arg Ile Ala Pro
        370                 375                 380

Val Gly Lys Thr Asp Leu Leu Ile Ile Arg Met Pro Lys Asp Phe Pro
385                 390                 395                 400

Pro Phe His Ser Arg Ala Arg Phe Arg Ala Met Lys Ala Gly Asp Lys
                405                 410                 415

Val Cys Met Ile Gly Val Asp Tyr Gln Glu Asn His Ile Ala Ser Lys
                420                 425                 430

Val Ser Glu Thr Ser Ile Ile Ser Glu Gly Thr Gly Asp Phe Gly Cys
        435                 440                 445

His Trp Ile Ser Thr Asn Asp Gly Asp Cys Gly Asn Pro Leu Val Ser
        450                 455                 460

Val Ser Asp Gly Phe Ile Val Gly Leu His Ser Leu Ser Thr Ser Thr
465                 470                 475                 480

Gly Asp Gln Asn Phe Phe Ala Lys Ile Pro Ala Gln Phe Glu Glu Lys
                485                 490                 495

Val Leu Arg Lys Ile Asp Asp Leu Thr Trp Ser Lys His Trp Ser Tyr
                500                 505                 510

Asn Ile Asn Glu Leu Ser Trp Gly Ala Leu Lys Val Trp Glu Ser Arg
        515                 520                 525

Pro Glu Ala Ile Phe Asn Ala Gln Lys Glu Val Asn Gln Leu Asn Val
        530                 535                 540

Phe Glu Gln Ser Gly Ser Arg Trp Leu Phe Asp Lys Leu His Gly Asn
545                 550                 555                 560

Leu Lys Gly Val Ser Ser Ala Pro Ser Asn Leu Val Thr Lys His Val
                565                 570                 575

Val Lys Gly Ile Cys Pro Leu Phe Arg Asn Tyr Leu Glu Cys Asp Glu
                580                 585                 590

Glu Ala Lys Ala
        595

(2) INFORMATION FOR SEQ ID NO:13:

(i) SEQUENCE CHARACTERISTICS:
        (A) LENGTH: 596 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:13:

Ser Ser Phe Ser Leu Leu Gly Val Ile Asn Thr Ile Gln Ser Arg Tyr
1               5                   10                  15

Leu Val Asp His Ser Val Glu Asn Ile Arg Lys Leu Gln Leu Ala Lys
                20                  25                  30

Ala Gln Ile Gln Gln Leu Glu Ala His Met Gln Glu Asn Asn Val Glu
        35                  40                  45

Asn Leu Ile Gln Ser Leu Gly Ala Val Arg Ala Val Tyr His Gln Ser
50                  55                  60

Val Asp Gly Phe Lys His Ile Lys Arg Glu Leu Gly Leu Lys Gly Val
65                  70                  75                  80

Trp Asp Gly Ser Leu Met Ile Lys Asp Ala Ile Val Cys Gly Phe Thr
                85                  90                  95
```

-continued

```
Met Ala Gly Gly Ala Met Leu Leu Tyr Gln His Phe Arg Asp Lys Phe
                100                 105                 110

Thr Asn Val His Val Phe His Gln Gly Phe Ser Ala Arg Gln Arg Gln
            115                 120                 125

Lys Leu Arg Phe Lys Ser Ala Ala Asn Ala Lys Leu Gly Arg Glu Val
        130                 135                 140

Tyr Gly Asp Asp Gly Thr Ile Glu His Tyr Phe Gly Glu Ala Tyr Thr
145                 150                 155                 160

Lys Lys Gly Asn Lys Lys Gly Lys Met His Gly Met Gly Val Lys Thr
                165                 170                 175

Arg Lys Phe Val Ala Thr Tyr Gly Phe Lys Pro Glu Asp Tyr Ser Tyr
            180                 185                 190

Val Arg Tyr Leu Asp Pro Leu Thr Gly Glu Thr Leu Asp Glu Ser Pro
        195                 200                 205

Gln Thr Asp Ile Ser Met Val Gln Asp His Phe Ser Asp Ile Arg Arg
    210                 215                 220

Lys Tyr Met Asp Ser Asp Ser Phe Asp Arg Gln Ala Leu Ile Ala Asn
225                 230                 235                 240

Asn Thr Ile Lys Ala Tyr Tyr Val Arg Asn Ser Ala Lys Ala Ala Leu
                245                 250                 255

Glu Val Asp Leu Thr Pro His Asn Pro Leu Lys Val Cys Asp Asn Lys
            260                 265                 270

Leu Thr Ile Ala Gly Phe Pro Asp Arg Glu Ala Glu Leu Arg Gln Thr
        275                 280                 285

Gly Pro Pro Arg Thr Ile Gln Val Asp Gln Val Pro Pro Ser Lys
    290                 295                 300

Ser Val His His Glu Gly Lys Ser Leu Cys Gln Gly Met Arg Asn Tyr
305                 310                 315                 320

Asn Gly Ile Ala Ser Val Val Cys His Leu Lys Asn Thr Ser Gly Lys
                325                 330                 335

Gly Lys Ser Leu Phe Gly Ile Gly Tyr Asn Ser Phe Ile Ile Thr Asn
            340                 345                 350

Arg His Leu Phe Lys Glu Asn Asn Gly Glu Leu Ile Val Lys Ser Gln
        355                 360                 365

His Gly Lys Phe Ile Val Lys Asn Thr Thr Thr Leu Gln Ile Ala Pro
    370                 375                 380

Val Gly Lys Thr Asp Leu Leu Ile Ile Arg Met Pro Lys Asp Phe Pro
385                 390                 395                 400

Pro Phe His Ser Arg Ala Arg Phe Arg Ala Met Lys Ala Gly Asp Lys
                405                 410                 415

Val Cys Met Ile Gly Val Asp Tyr Gln Glu Asn His Ile Ala Ser Lys
            420                 425                 430

Val Ser Glu Thr Ser Ile Ile Ser Glu Gly Thr Gly Asp Phe Gly Cys
        435                 440                 445

His Trp Ile Ser Thr Asn Asp Gly Asp Cys Gly Asn Pro Leu Val Ser
    450                 455                 460

Val Ser Asp Gly Phe Ile Val Gly Leu His Ser Leu Ser Thr Ser Thr
465                 470                 475                 480

Gly Asp Gln Asn Phe Phe Ala Lys Ile Pro Ala Gln Phe Glu Glu Lys
                485                 490                 495

Val Leu Arg Lys Ile Asp Asp Leu Thr Trp Ser Lys His Trp Ser Tyr
            500                 505                 510

Asn Ile Asn Glu Leu Ser Trp Gly Ala Leu Lys Val Trp Glu Ser Arg
```

```
              515                 520                 525
Pro Glu Ala Ile Phe Asn Ala Gln Lys Glu Val Asn Gln Leu Asn Val
    530                 535                 540

Phe Glu Gln Ser Gly Gly Arg Trp Leu Phe Asp Lys Leu His Gly Asn
545                 550                 555                 560

Leu Lys Gly Val Ser Ser Ala Pro Ser Asn Leu Val Thr Lys His Val
                565                 570                 575

Val Lys Gly Ile Cys Pro Leu Phe Arg Asn Tyr Leu Glu Cys Asp Glu
                580                 585                 590

Glu Ala Lys Ala
            595
```